(12) United States Patent
Chan et al.

(10) Patent No.: US 9,307,968 B2
(45) Date of Patent: Apr. 12, 2016

(54) MATERIALS AND METHODS FOR FILLING BIOLOGICAL CAVITIES AND PREVENTING LEAKAGE OF INJECTED THERAPEUTIC AGENTS

(71) Applicant: THE UNIVERSITY OF HONG KONG, Hong Kong (CN)

(72) Inventors: Barbara Pui Chan, Hong Kong (CN); Tsz Kit Chik, Hong Kong (CN); Tsz Hang Andrew Choy, Hong Kong (CN); Xuanyi Ma, Hong Kong (CN); K. M. C. Cheung, Hong Kong (CN)

(73) Assignee: The University of Hong Kong, Hong Kong (CN)

(*) Notice: Subject to any disclaimer, the term of this patent is extended or adjusted under 35 U.S.C. 154(b) by 0 days.

(21) Appl. No.: 13/916,982

(22) Filed: Jun. 13, 2013

(65) Prior Publication Data
US 2013/0338636 A1    Dec. 19, 2013

Related U.S. Application Data

(60) Provisional application No. 61/660,385, filed on Jun. 15, 2012.

(51) Int. Cl.
*A61B 17/00* (2006.01)
*A61M 5/31* (2006.01)
*A61B 17/34* (2006.01)
(Continued)

(52) U.S. Cl.
CPC ....... *A61B 17/0057* (2013.01); *A61B 17/00491* (2013.01); *A61B 17/34* (2013.01); *A61L 27/20* (2013.01); *A61L 27/24* (2013.01); *A61L 27/3834* (2013.01); *A61L 27/50* (2013.01); *A61L 27/54* (2013.01); *A61M 5/31* (2013.01); *A61B 2017/00893* (2013.01); *A61L 2300/64* (2013.01); *A61L 2400/06* (2013.01)

(58) Field of Classification Search
CPC ............... A61B 17/70; A61B 17/3417; A61F 2002/4435; A61F 2002/444; A61F 2/4405; A61F 2/441; A61F 2/442; A61M 5/16813; A61M 5/3216; A61M 37/0069; A61M 39/28; A61M 2039/0276; A61M 2005/3103; A61M 2005/3107; A61M 2005/3109; A61M 2005/311; A61M 2005/3117; A61M 2005/3118; A61M 2005/312; A61M 39/10; A61M 39/12; A61M 39/20; A61M 39/22; A61M 39/284; A61M 39/288
USPC ............... 606/151, 214, 213, 192; 623/23.72, 623/23.75, 23.76, 17.11–17.12; 424/424, 424/425, 443, 444, 449
See application file for complete search history.

(56) References Cited

U.S. PATENT DOCUMENTS 5,489,274 A * 2/1996 Chu et al. ................. 604/167.05
6,248,110 B1 * 6/2001 Reiley et al. .................... 606/93
(Continued)

OTHER PUBLICATIONS

Zhao et al., "The cell biology of intervertebral disc aging and degeneration", *Ageing Res Rev.* 2007, vol. 6, pp. 247-261.
(Continued)

*Primary Examiner* — Ryan J Severson
*Assistant Examiner* — Rachel S Papeika
(74) *Attorney, Agent, or Firm* — Leason Ellis LLP

(57) ABSTRACT

The subject invention pertains to medical apparatuses and methods for reducing or preventing leakage of injected therapeutic agents (including liquid-containing substances, cells) into a solid or hollow tissue/organ after puncturing.

6 Claims, 16 Drawing Sheets

Figure 2A:
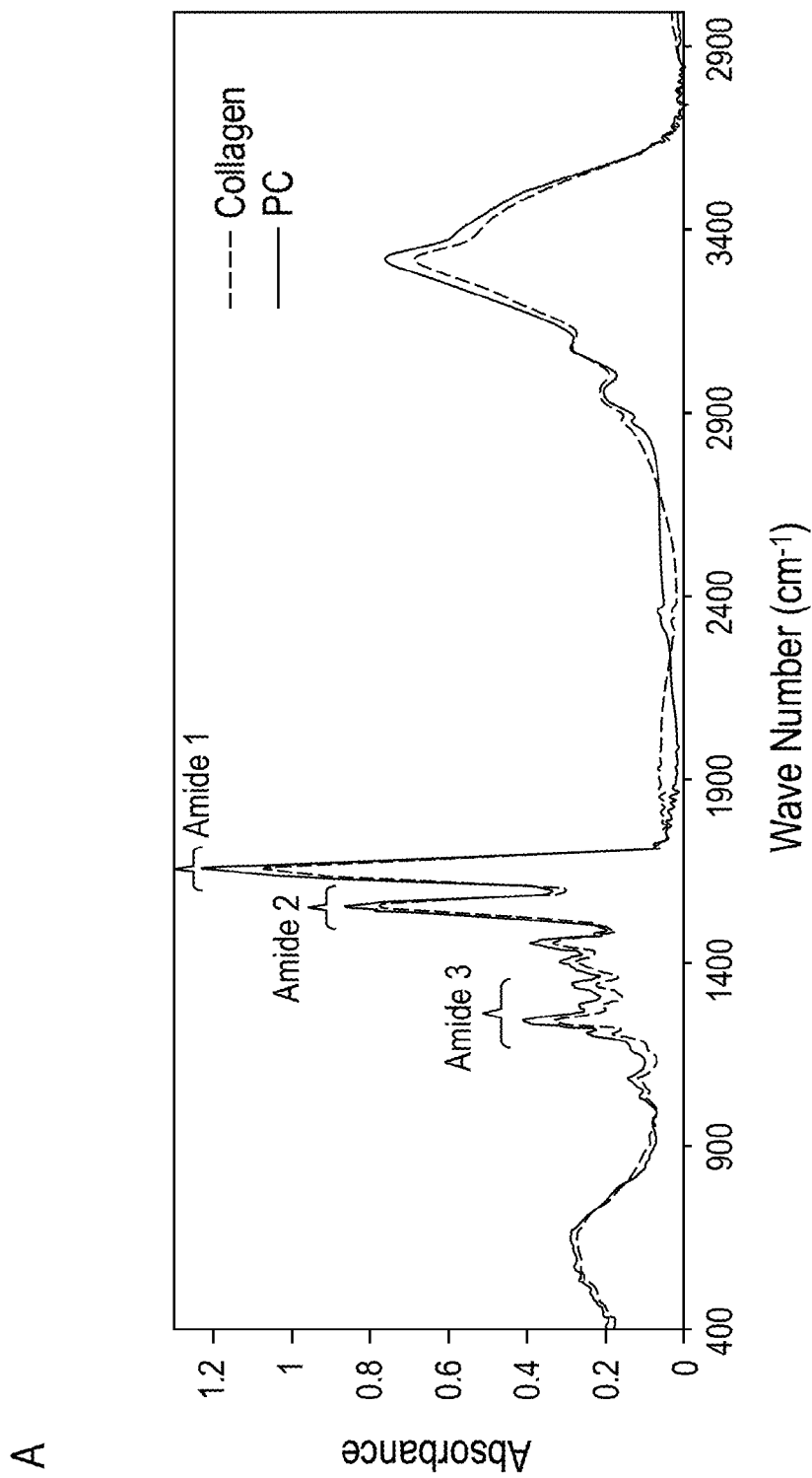
Figure 2B:
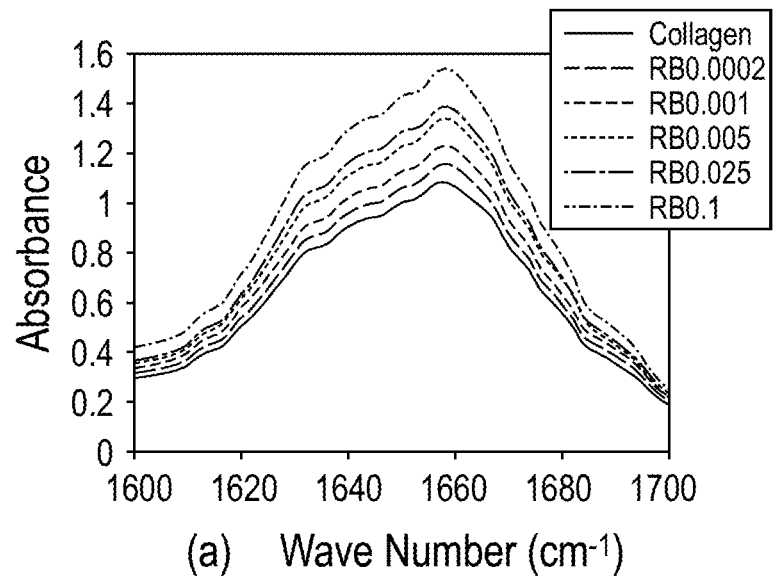

(51) Int. Cl.
  A61L 27/20  (2006.01)
  A61L 27/24  (2006.01)
  A61L 27/38  (2006.01)
  A61L 27/50  (2006.01)
  A61L 27/54  (2006.01)

(56) References Cited

U.S. PATENT DOCUMENTS

| | | | |
|---|---|---|---|
| 6,419,704 | B1 | 7/2002 | Ferree |
| 6,592,625 | B2 | 7/2003 | Cauthen |
| 6,883,520 | B2 | 4/2005 | Lambrecht et al. |
| 7,393,437 | B2 | 7/2008 | Chan et al. |
| 7,931,918 | B2 | 4/2011 | Chan et al. |
| 2002/0029083 | A1* | 3/2002 | Zucherman et al. ....... 623/17.16 |
| 2006/0004326 | A1* | 1/2006 | Collins et al. .................... 604/57 |
| 2008/0221605 | A1* | 9/2008 | Saal et al. ...................... 606/170 |
| 2010/0030160 | A1* | 2/2010 | Glocker ......................... 604/221 |
| 2012/0010653 | A1* | 1/2012 | Seifert et al. .................. 606/213 |

OTHER PUBLICATIONS

Freimark et al., "Cell-based regeneration of intervertebral disc defects: Review and concepts", *The International Journal of Artificial Organs*, 2009, vol. 32(4), pp. 197-203.
Zhang et al., "Bone mesenchymal stem cells transplanted into rabbit intervertebral discs can increase proteoglycans", *Clin Orthop Relat Res.*, 2005, vol. 430, pp. 219-226.
Leung et al., "Regeneration of intervertebral disc by mesenchymal stem cells: potentials, limitations, and future direction", *Eur Spine J.*, 2006, vol. 15 (Suppl.), pp. S406-S413.
Vadalà et al. "Coculture of bone marrow mesenchymal stem cells and nucleus pulposus cells modulate gene expression profile without cell fusion", *Spine*, 2008, vol. 33(8), pp. 870- 876.
Yoshikawa et al., "Disc Regeneration Therapy Using Marrow Mesenchymal Cell Transplantation a Report of Two Case Studies", *Spine*, 2010, vol. 35, pp. E475-E480.
Bertram et al., "Matrix-assisted cell transfer for interverte-bral disc cell therapy" *Biochem Biophys Res Commun.*, 2005, vol. 331, pp. 1185-1192.
Sakai et al., "Transplantation of mesenchymal stem cells embedded in Atelocollagen gel to the intervertebral disc: a potential therapeutic model for disc degeneration", *Biomaterials*, 2003, vol. 24, pp. 3531-3541.
Sakai et al., "Differentiation of mesenchymal stem cells transplanted to a rabbit degenerative disc model: potential and limitations for stem cell therapy in disc regeneration", *Spine*, Nov. 1, 2005, vol. 30(21), pp. 2379-2387.
Sykova et al., "Bone Marrow Stem Cells and Polymer Hydrogels—Two Strategies for Spinal Cord Injury Repair", *Cellular and Molecular Neurobiology*, Oct./Nov. 2006, pp. 1113-1129.
Sobajima et al. "Feasibility of a stem cell therapy for intervertebral disc degeneration", *Spine J.*, 2008; vol. 8(6), pp. 888-896.
Roberts et al., "Bovine explant model of degeneration of the intervertebral disc", *BMC Musculoskelet Disord*, 2008, vol. 9:24 pp. 1-6.
Vadala et al., "Mesenchymal stem cells injection in degenerated intervertebral disc: cell leakage may induce osteophyte formation", *J Tissue Eng Regen Med*, 2011, DOI:10.1002/term.433, pp. 348-355.
Sobajima et al., "A slowly progressive and reproducible animal model of intervertebral disc degeneration characterized by MRI, X-ray, and histology" *Spine*, 2004, vol. 30, pp. 15-24.
Chan et al., "Photochemical crosslinking improves the physicochemical properties of collagen scaffolds", *J Biomed Mater Res A*, 2005, vol. 75, pp. 689-701.
Chan et al. "Photochemical cross-linking for collagen-based scaffolds: a study on optical properties, mechanical properties, stability, and hematocompatibility", *Tissue eng.*, 2007, vol. 13, pp. 73-85.
Kong et al., "Fourier transform infrared spectroscopic analysis of protein secondary structures", *Acta Biochim Biophys Sin.*, 2007, vol. 39, pp. 549-559.
Chang et al., "FT-IR study for hydroxyapatite/collagen nanocomposite cross-linked by glutaraldehyde", *Biomaterials*, 2002, vol. 23, pp. 4811-4818.

Wang et al., "Biologic response of the intervertebral disc to static and dynamic compression in vitro", *Spine*, 2007, vol. 32, pp. 2521-2528.
Ching et al., "Changes in nuclear composition following cyclic compression of the intervertebral disc in an in vivo rat-tail model", *Med Eng Phys.*, 2004, vol. 26, pp. 587-594.
Masuoka et al., "Different effects of static versus cyclic compressive loading on rat intervertebral disc height and water loss in vitro", *Spine*, 2007, vol. 32, pp. 1974-1979.
MacLean et al., "The effects of short-term load duration on anabolic and catabolic gene expression in the rat tail intervertebral disc", *J Orthop Res.*, 2005, vol. 23, pp. 1120-1127.
MacLean et al., "Anabolic and catabolic mRNA levels of the intervertebral disc vary with the magnitude and frequency of in vivo dynamic compression", *J Orthop Res.* 2004, vol. 22, pp. 1193-1200.
Illien-Junger et al., "The Combined Effects of LimitedNutrition and High-Frequency Loading on Intervertebral Discs With Endplates", *Spine*, 2010, vol. 35(19), pp. 1744-1752.
Heuer et al., "Biomechanical evaluation of conventional anulus fibrosus closure methods required for nucleus replacement. Laboratory investigation", *J Neurosurg Spine*, 2008, vol. 9, pp. 307-313.
Di Martino et al., "Nucleus pulposus replacement: basic science and indications for clinical use", *Spine*, 2005, vol. 30, pp. S16-22.
Raj, "Intervertebral disc: anatomy-physiology-pathophysiology-treatment", *Pain Pract.*, 2008, vol. 8, pp. 18-44.
Risbud et al., "Differentiation of mesenchymal stem cells towards a nucleus pulposus-like phenotype in vitro: implications for cell-based transplantation therapy", *Spine*, 2004, vol. 29m pp. 2627-2632.
Yang et al., "Mesenchymal stem cells arrest intervertebral disc degeneration through chondrocytic differentiation and stimulation of endogenous cells", *Mol Ther.*, 2009, vol. 17, pp. 1959-1966.
Crevensten et al., "Intervertebral disc cell therapy for regeneration: mesenchymal stem cell implantation in rat intervertebral discs", *Ann Biomed Eng.*, 2004, vol. 32(3), pp. 430-434.
Sakai et al., "Regenerative effects of transplanting mesenchymal stem cells embedded in atelocollagen to the degenerated intervertebral disc", *Biomaterials*, 2006, vol. 27, pp. 335-345.
Cheung et al., "Regeneration of nucleus pulposus after discectomy by autologous mesenchymal stem cells: a rabbit model", *Eur Cell Mater.* 2005, vol. 10, pp. 52.
Miyamoto T, et al., "Intradiscal transplantation of synovial mesenchymal stem cells prevents intervertebral disc degeneration through suppression of matrix metalloproteinase-related genes in nucleus pulposus cells in rabbits", *Arthritis Res Ther.*, 2010, vol. 12, pp. R206.
Benz et al., "Intervertebral disc cell- and hydrogel-supported and spontaneous intervertebral disc repair in nucleotomized sheep", *Eur Spine J.*, 2012, vol. 21(9), pp. 1758-1768.
Acosta et al., "Porcine intervertebral disc repair using allogeneic juvenile articular chondrocytes or mesenchymal stem cells", *Tissue eng Part A.*, 2011, vol. 17, pp. 3045-3055.
Schek et al., "Genipin-crosslinked fibrin hydrogels as a potential adhesive to augment intervertebral disc annulus repair", *Eur Cell Mater.* 2011, vol. 21, pp. 373-383.
Chan "Biomedical applications of photochemistry", *Tissue Eng Part B Rev.*, 2010, vol. 16, pp. 509-522.
Cheng et al., "In vitro generation of an osteochondral interface from mesenchymal stem cell-collagen microspheres", *Biomaterials*, 2011, vol. 32, pp. 1526-1535.
Henriksson et al., "Transplantation of human mesenchymal stems cells into intervertebral discs in a xenogeneic porcine model", *Spine*, 2009, vol. 34, pp. 141-148.
Ho et al., "Effect of severity of intervertebral disc injury on mesenchymal stem cell-based regeneration", *Connect Tissue Res.*, 2008, vol. 49, pp. 15-21.
Chujo et al., "Effects of growth differentiation factor-5 on the intervertebral disc—in vitro bovine study and in vivo rabbit disc degeneration model study", *Spine*, 200, vol. 31, pp. 2909-2917.
Cripton et al., "A minimally disruptive technique for measuring intervertebral disc pressure in vitro: application to the cervical spine", *J Biomech.*, 2001, vol. 34, pp. 545-549.
Gorensek et al., "Nucleus pulposus repair with cultured autologous elastic cartilage derived chondrocytes", *Cell Mol Biol Lett.*, 2004, vol. 9, pp. 363-373.

(56) References Cited

OTHER PUBLICATIONS

Bergknut et al. "The performance of a hydrogel nucleus pulposus prosthesis in an ex vivo canine model", *Biomaterials.*, 2010, vol. 31, pp. 6782-6788.

Choy et al., "Chemical modification of collagen improves glycosaminoglycan retention of their co-precipitates", *Acta Biomater.*, 2013, vol. 9, pp. 4661-4672.

* cited by examiner

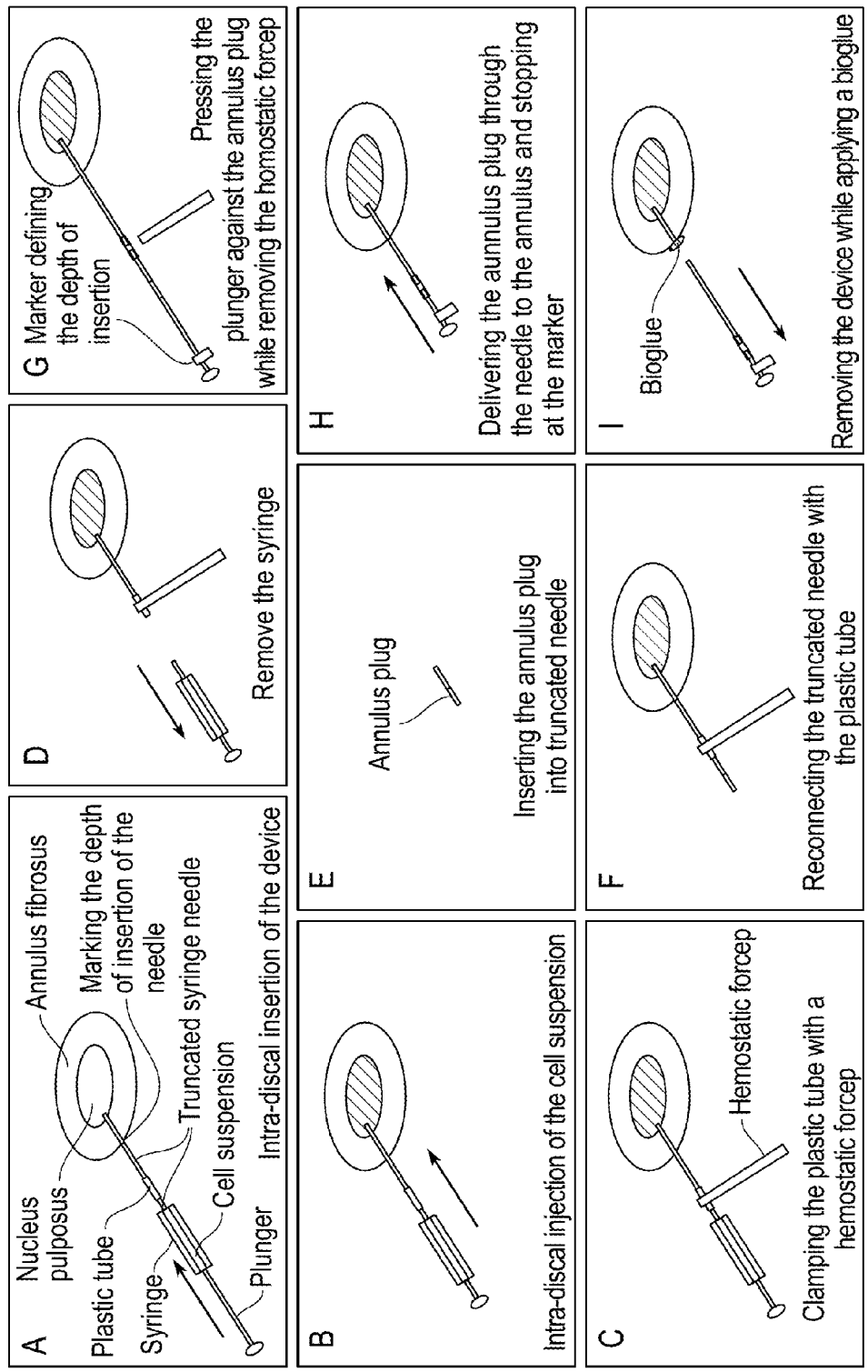
Fig. 1 (A-I)

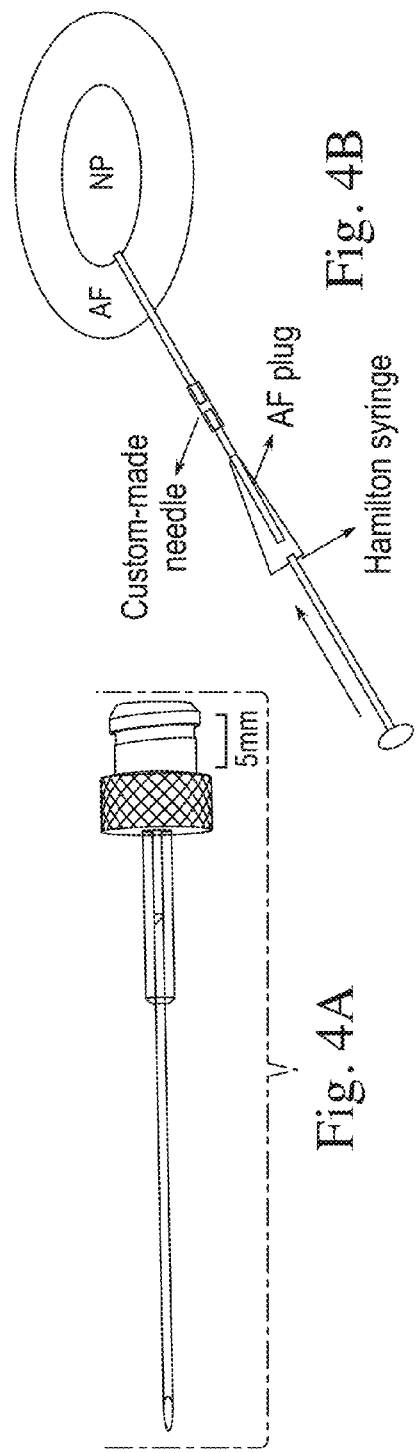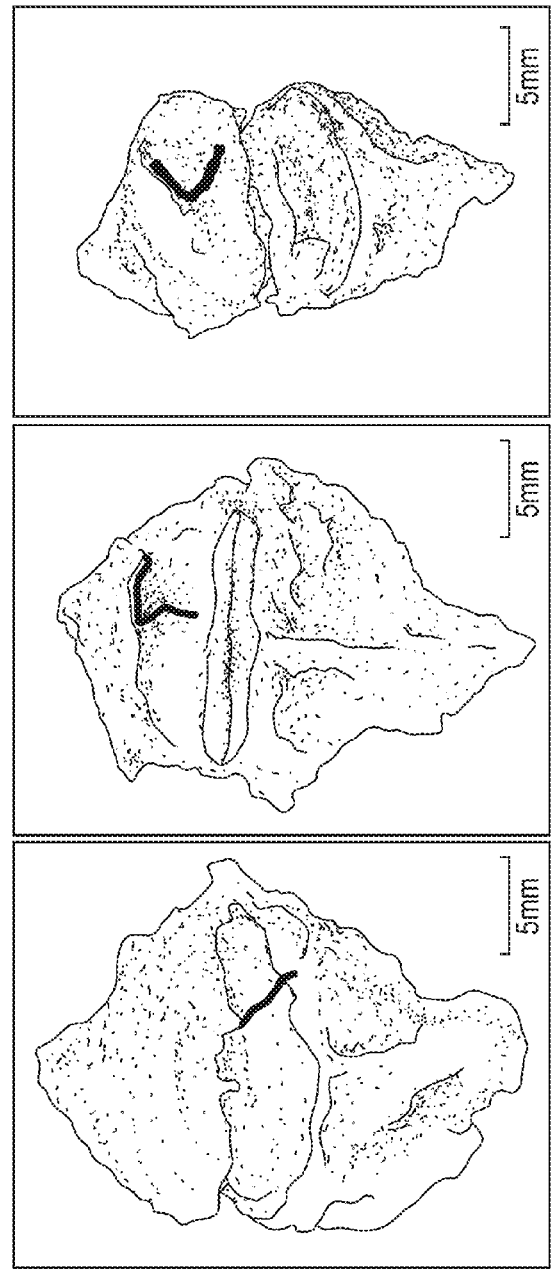
Fig. 4A Fig. 4B Fig. 4C Fig. 4D Fig. 4E

| Parameter | Compression test | Torsion test |
|---|---|---|
| Syringe Gauge | 21G | 21G |
| Frequency | 0.2Hz | 0.2Hz |
| Load | Active cyclic loading phase from 0.4 to 0.8MPa, followed by resting phase at 0.2MPa for 8 hours, for 7 days | Active cyclic loading phase from 0 to 25 degree angular displacement, followed by resting phase at 0 degree for 8 hours, for 7 days |
| Cycles tested | 40,320 | 40,320 |
| Sample Size | 4 | 3 |
| Result | All annulus plugs were still intact after the test | All annulus plugs were still intact after the test |

Fig. 5H  Fig. 5I

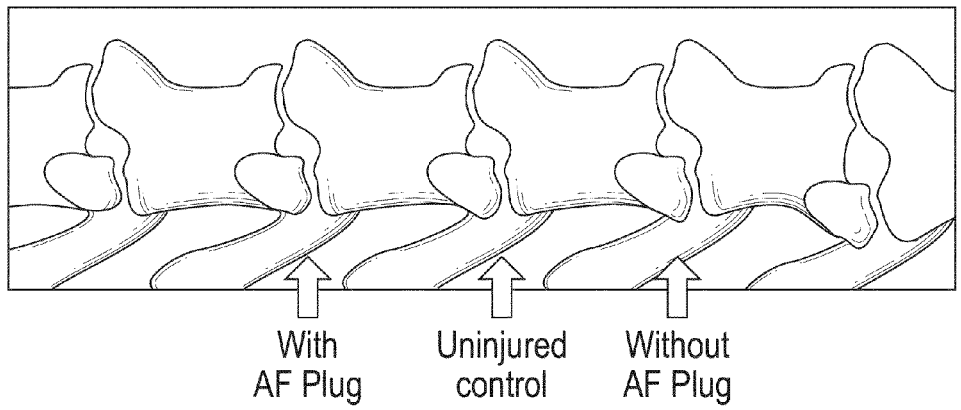
Fig. 7A
| B | Osteophyte (+) | Osteophyte (−) |
|---|---|---|
| With annulus plug | 0 | 9 |
| Uninjured control | 0 | 9 |
| Without annulus plug | 2 | 7 |
Fig. 7B
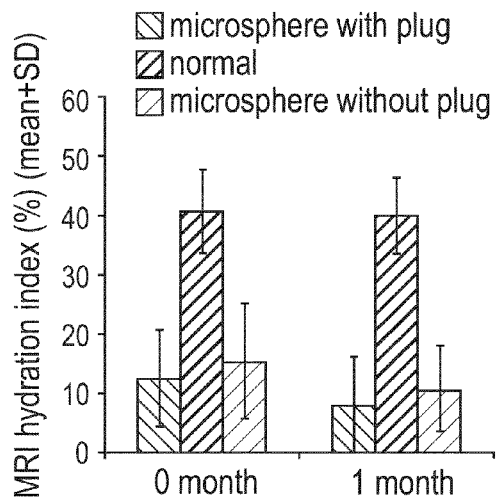
Fig. 7C
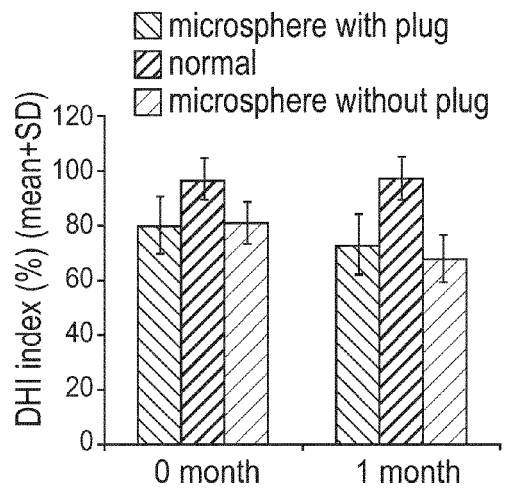
Fig. 7D Fig. 7E
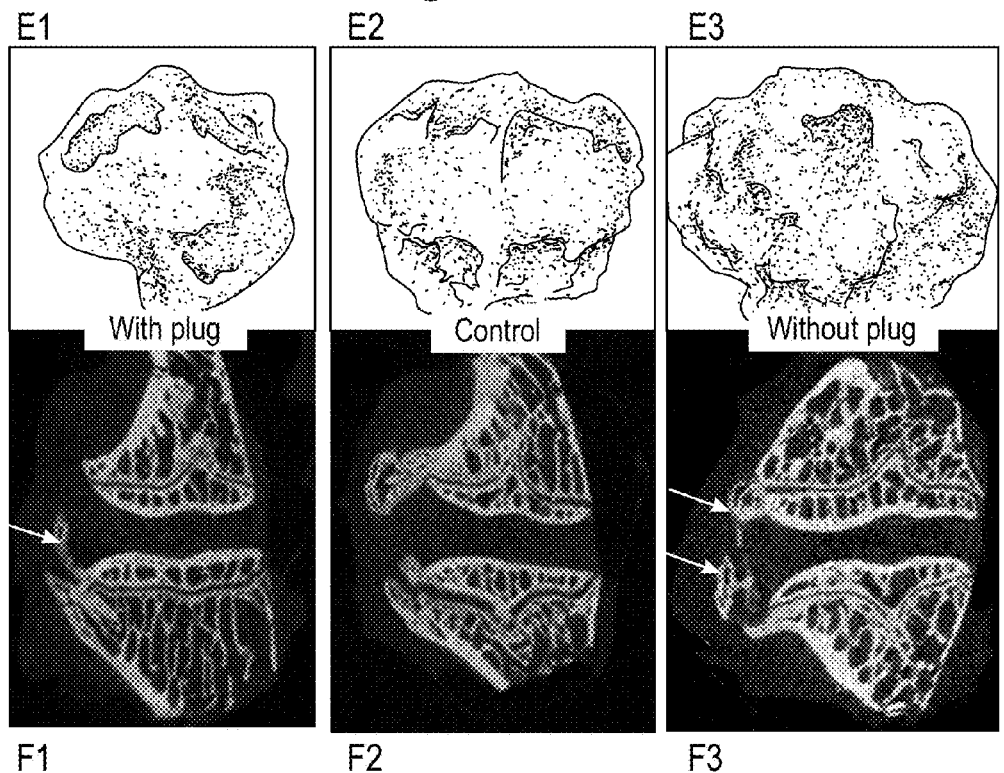
Fig. 7F
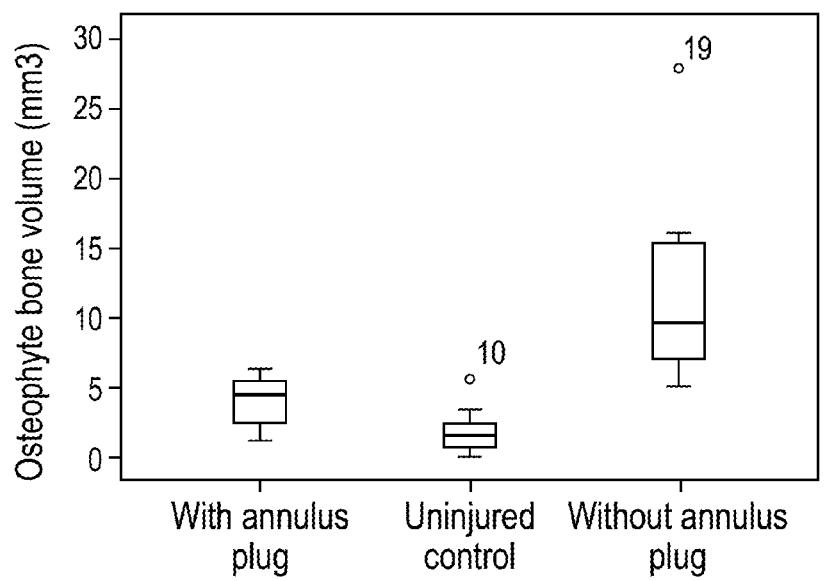
Fig. 7G

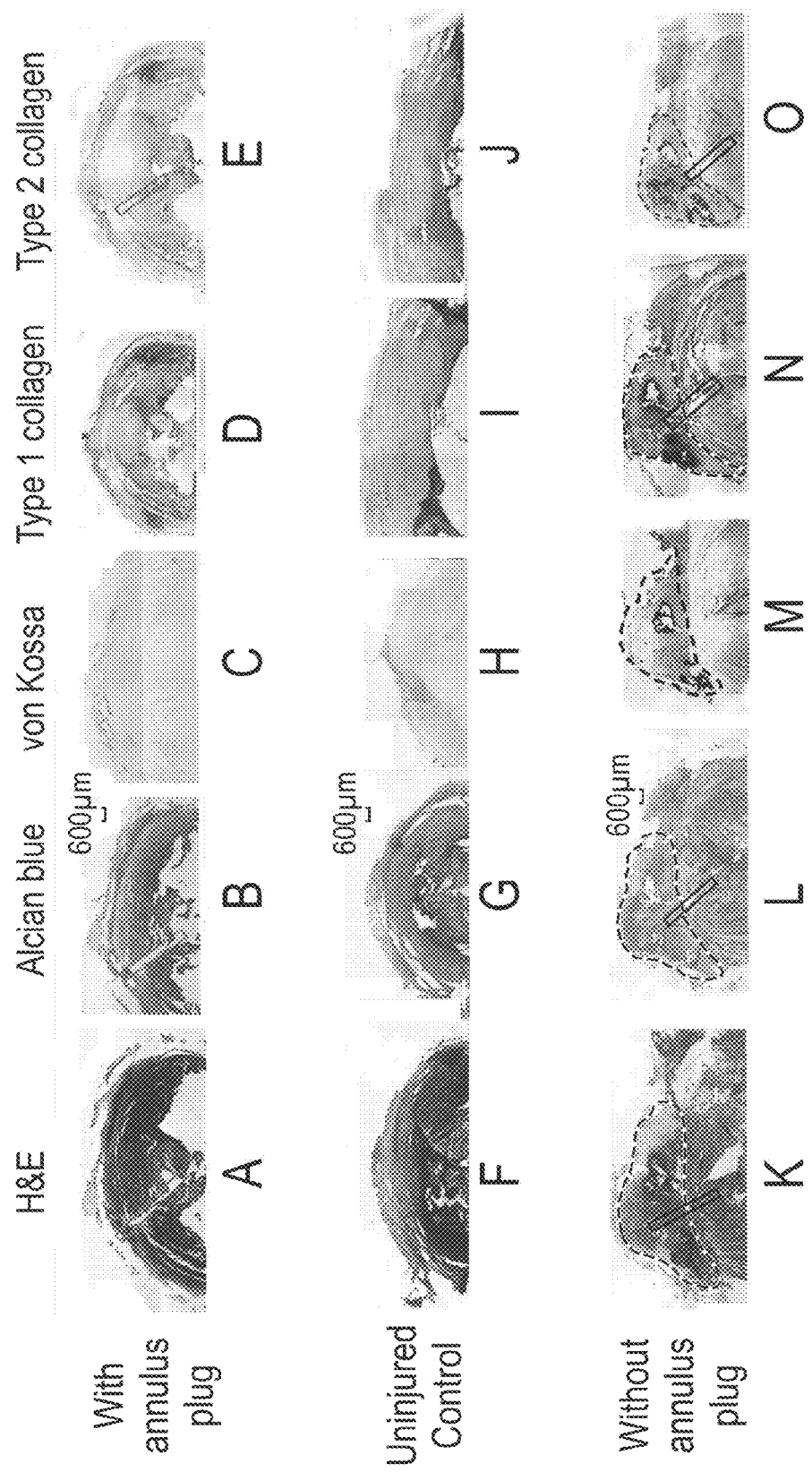
Fig. 8 (A-O)

MATERIALS AND METHODS FOR FILLING BIOLOGICAL CAVITIES AND PREVENTING LEAKAGE OF INJECTED THERAPEUTIC AGENTS

This application claims the benefit of U.S. provisional application Ser. No. 61/660,385, filed Jun. 15, 2012, which is hereby incorporated by reference in its entirety.

1. FIELD

The present invention relates generally to materials and methods for preventing cell suspensions, fluids, mixtures, and gelatinous substances from leaking after injection into soft tissue or intervertebral discs (IVD).

2. BACKGROUND

Injection of biomolecules, genes and cells is commonly used in biological therapies. For example, intra-discal injection of biomolecules such as transforming growth factor-beta 1 has been used in the treatment of degenerative intervertebral discs (IVD) (Zhao et al.; 2007). In addition, direct transfection of disc cells in vivo, as well as transfection of disc cells in vitro followed by the return of the transfected cells back to the disc, has been used in gene therapy (Freimark et al., 2009).

Recently, mesenchymal stem cell (MSC)-based therapy for treating degenerative discs has received much attention (Freimark et al., 2009). Many animal models have demonstrated the value of mesenchymal stem cell (MSC)-based therapy for treating degenerative discs. Long term survival of MSCs has been demonstrated in a rabbit model (Zhang et al., 2005). Effective arrest of disc degeneration has also been demonstrated in rabbit and canine models (Leung et al., 2006; Vadala et al., 2008). Early phase clinical trials also reported that mesenchymal stem cell (MSC)-based therapy produces encouraging results in alleviating symptoms and improving disc stability (Yoshikawa et al., 2010).

A critical problem common to all intra-discal injection is the leakage or backflow of the injected materials through the injection portal caused by the large intra-discal pressure. Matrix-assisted cell delivery has been proposed; however, only fewer than the 3% of the injected cells were found in the disc after injection (Bertram et al., 2005). Hydrogels made of natural biomaterials such as hyaluronan gel and atellocollagen as well as hydrogels made of synthetic biomaterials such as 2-hydroxyethyl methacrylate have been used in intra-discal injection (Sakai et al. 2003; Sakai et al., 2005; Sykova et al, 2006). However, hydrogels usually have insufficient viscosity and stiffness; this results in an immediate loss of a majority of injected cells (>96%) due to the backflow of the injected materials via the injection path. The problem of leakage or backflow of injected materials is reported in a degenerative IVD model in rat, and is observed by the present inventors using hydrogel or collagen microspheres as injection materials. The current cell-based therapy results in low cell retention inside the disc, a significant cell leakage, the formation of osteophytes, and the lack of adequate amount of MSCs inside the disc (Sobajima et al., 2008; Roberts et al., 2008; Vadala et al., 2011; Sobajima et al., 2004). Moreover, the formation of osteophyte may attribute to cell leakage as the presence of MSCs was demonstrated within the osteophyte tissue (Vadala et al., 2011).

The leakage of injected cells and other biomaterials negatively affects the safety and efficacy of cell-based therapy in disc degeneration. There is a need of developing improved devices for preventing leakage of injected materials in biological therapy.

3. SUMMARY

In one embodiment, the present invention provides a medical apparatus for filling an unwanted or artificially-created space or cavity, or for closing an unwanted or artificially-created opening inside the body of a subject, wherein the apparatus comprises a filling device that can be delivered into an unwanted or artificially-created space or cavity inside the body of a subject, wherein the filling device is adapted to take the shape that can substantially fill the unwanted or artificially-created space or cavity, or can substantially close the unwanted or artificially-created opening, wherein the filling device is preferably made of biocompatible material.

In one embodiment, the unwanted or artificially-created space, cavity, or opening is created by the injection of a therapeutic agent into a target site of the body of a subject. Therapeutic agents in accordance with the present invention include, but are not limited to, drugs, cells, and genes.

In one embodiment, the filling device is a plug (e.g., an annulus plug).

In one embodiment, the medical apparatus further comprises a sealing material. In one embodiment, the sealing material is a biocompatible adhesive.

In another embodiment, the present invention provides a method for filling an unwanted or artificially-created space or cavity, or for closing an unwanted or artificially-created opening inside the body of a subject, wherein the method comprises: delivering a filling device to an unwanted or artificially-created space or cavity inside the body of a subject, wherein the filling device is adapted to take the shape that can substantially fill the unwanted or artificially-created space or cavity, or can substantially close the unwanted or artificially-created opening, wherein the filling device is preferably made of biocompatible material.

In another embodiment, the present invention provides a method for preventing leakage of an injected therapeutic agent from a target site of injection within the body of a subject, wherein the method comprises:

injecting a composition comprising a therapeutic agent, and optionally, a pharmaceutically-acceptable carrier, into a target site of the body, wherein the injection creates an unwanted or artificially-created space or cavity inside the body; and delivering a filling device to the unwanted or artificially-created space or cavity, wherein the filling device is adapted to take the shape that can substantially fill the unwanted or artificially-created space or cavity, or can substantially close the unwanted or artificially-created opening, wherein the filling device is preferably made of biocompatible material.

3.1 Definitions

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

4. BRIEF DESCRIPTION OF THE DRAWINGS

FIGS. 1(A-I) are schematic drawings showing an embodiment of the medical apparatus of the present invention as well as an embodiment of the method of delivering the annulus plug after injection of cells in intervertebral discs (IVD).

FIGS. 2(A-M) show FTIR spectra analysis of collagen samples. A: Wide scan spectrum; B-E: Amide I spectrum analysis; F-I: Amide II spectrum analysis; J-M: Amide III spectrum analysis; B, F & J: Rose Bengal dose dependent changes in Amide I, II and III spectra; C, G & K: Laser fluence dose dependent changes in Amide I, II and III spectra; D, H & L: Rose Bengal dose dependent changes in peak absorbance for Amide I, peak frequency in Amide II and peak absorbance ratio in Amide III, respectively; E, I & M: Laser fluence dose dependent changes in peak absorbance in Amide I, peak frequency in Amide II and peak absorbance ratio in Amide III, respectively. For rose Bengal dose dependence study, laser fluence was fixed at 10 $J/cm^2$ while for laser fluence dose dependence study, rose Bengal concentration was fixed at 0.001% (w/v). (n=5-6).

FIGS. 3(A-E) show physical characterization of annulus plug. A: Gross appearance of annulus plug (scale bar: 200 µm); B: SEM image showing the surface of annulus plug (magnification: 10KX; scale bar: 200 µm); C: SEM images showing the cross-sections of annulus plug (magnification: 8K×; scale bar: 200 µm); D: Distribution of the diameter of the annulus plug fabricated; E: Swelling index of annulus plug fabricated with 0.001% (w/v) rose Bengal and 12.5 J/cm2 laser fluence (n=8).

FIGS. 4(A-E) show annulus plug delivery and placement. A: Gross appearance of the annulus plug and the modified 21G Hamilton syringe needle used for delivery; B: Schematic diagram illustrating the delivery of the annulus plug into the disc (AF: annulus fibrosus; NP: nucleus pulposus); C-E: Dissected rabbit intervertebral disc showing successful placements of annulus plugs. C: Desired positioning right into the AF; D: Bending of the plug; E: Extension of the plug into the NP region. (Scale bars: 5 mm)

FIGS. 5(A-I) show ex vivo mechanical tests of annulus plug. A: Annulus plug blocking the injection portal at the annulus fibrosus; B: Sample mounted on loading stage for compression; C: Sample after compression loading; D: Compression or torsion loading in bioreactor; E: Sample after torsion loading; F: Loading regime showing pressure versus time; G: Loading regime showing torque versus time; H: Compression loading parameters; I: Torsion loading parameters. (n=4 for compression, n=3 for torsion)

FIGS. 6(A-F) show ex vivo leakage test. A: Rabbit IVD injected with MSC-collagen microspheres with or without the annulus plug was mounted onto the chamber of a bioreactor; B: Samples were exposed to the same compression loading regime used in the ex vivo push-out test; C: Confocal microscopy of Alexa 488-labeled MSC-collagen microspheres before injection; D: Fluorescent MSC-collagen microspheres retrieved from the NP cavity after 7 days of compression loading; E: Representative standard curve constructed correlating the fluorescence signal with the number of MSC-collagen microspheres (n=2); F: Bar chart showing the mean percentage of fluorescence-labelled microspheres trapped in the void volume of the syringe on day 0, leaked out in the culture medium during 7 days of compression, and retained in the NP cavity after 7 days of compression (n=3).

FIGS. 7(A-G) show radiographical evaluation of degenerative discs repaired with MSCs in collagen microsphere carriers with and without annulus plugs. A: Representative x-ray radiographs of different levels of involved discs; B: Contingency table showing frequency of osteophyte formation based on x-ray radiograph and gross morphology assessment; C: MRI hydration index (n=9); D: x-ray disc height index (n=9); E1-3: Representative gross appearance of involved discs in groups with annulus plug (E1), of uninjured control (E2) and without annulus plug (E3); F1-F3: Representative images of microCT volumetric analysis of involved discs in groups with annulus plug (F1), of uninjured control (F2) and without annulus plug (F3) (white arrows: sites of osteophyte formation); G: Contingency table showing frequency of osteophyte formation based on microCT volumetric analysis; H: Box plot showing the osteophyte volume measured by microCT in different groups (n=9).

FIGS. 8(A-O) show histological and inununohistochemical characterization of disc matrix and osteophyte markers in different treatment groups. A-E: With annulus plug; F-J: Uninjured control; K-O: Without annulus plug; A, F, K: H&E staining for morphology; B, G, L: Alcian blue staining for GAGs; C, H, M: von Kossa staining for calcium deposits; D, I, N: Type I collagen immunohistochemistry; E, J, O: Type II collagen immunohistochemistry. (Solid rectangular frame: Injection portal; Dotted line: osteophyte)

5. DETAILED DESCRIPTION

Intra-discal injection of mesenchymal stem cells (MSCs) in treating disc degeneration may lead to unfavorable complication particularly osteophyte formation. Development of an effective method to block the injection portal, prevent the leakage of injected cells and materials and hence prevent osteophyte formation is of utmost importance before clinical translation of MSC-based therapy. Provided herein is a solution to alleviate the cell leakage problem and the associated complication osteophyte formation an injectable annulus plug to block the injection portal during intra-discal delivery. Specifically, a needle-shaped collagen plug is provided herein by photochemical crosslinking and successfully delivered it intra-discally, in adjunct with MSCs in collagen microsphere carriers, using a custom-made delivery device. The mechanical performance of the plug and its effectiveness in reducing cell leakage were evaluated ex vivo under compression and torsion push-out tests. Results demonstrated that the plug survived physiologically relevant loading and significantly reduced leakage and enhanced retention of the injected materials. MicroCT imaging and histology revealed that the plug significantly reduced osteophyte formation. Provided herein is an annulus plug that is used as an adjunct or annulus closure device upon intra-discal delivery of cells and materials.

In one embodiment, the present invention provides a medical apparatus for filling an unwanted or artificially-created space or cavity, or for closing an unwanted or artificially-created opening inside the body of a subject, wherein the apparatus comprises a filling device that can be delivered into an unwanted or artificially-created space or cavity inside the body of a subject, wherein the filling device is adapted to take the shape that can substantially fill the unwanted or artificially-created space or cavity, or can substantially close the unwanted or artificially-created opening, wherein the filling device is preferably made of biocompatible material.

In one embodiment, the unwanted or artificially-created space, cavity, or opening is created by the injection of a therapeutic agent into a target site of the body of a subject. Therapeutic agents in accordance with the present invention include, but are not limited to, drugs, cells, and genes.

In one embodiment, the filling device has a size that is smaller than the size of the unwanted or artificially-created internal space, cavity, or opening before the filling device is delivered to the space, cavity, or opening; and once the filling device is delivered to the unwanted or artificially-created internal space, cavity, or opening, the filling device can expand into a shape that is substantially the same as that of the internal space, cavity, or opening to be filled.

In one embodiment, the filling device fills the cavity created in the course of delivery of a therapeutic agent into a target site of the body.

As used herein, substantially filling a space or cavity, or substantially closing an opening means that greater than 80% (including greater than 85%, 90%, 95%, 97%, 99%) of the internal space, cavity, or opening is filled or closed.

The term "subject," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; and other animals such as dogs, cats, horses, cattle, pigs, sheep, goats, chickens, mice, rats, guinea pigs, and hamsters.

In one embodiment, the medical apparatus is for use in a cell-based or a biological therapy. In one embodiment, in the course of delivering a therapeutic agent (e.g., cells, drugs, genes) into a target site (e.g., tissue or organ) within a subject, tissue(s) and/or organ(s) of the subject are punctured, thereby creating an internal space, cavity, or portal that could result in the leakage of the therapeutic agent from the target site. The medical apparatus of the present invention reduces and/or prevents leakage of the therapeutic agent from the target site of delivery. In one embodiment, the filling device is capable of taking the shape of an internal cavity of an injection needle or an internal space or cavity to be filled. In one embodiment, the filling device possesses physicochemical properties so that once the filling device occupies an internal space or cavity, it can withstand physiological challenges.

In one embodiment, the filling device is a plug (e.g., an annulus plug).

In one embodiment, the medical apparatus further comprises a sealing material. In one embodiment, the sealing material is a biocompatible adhesive.

In one embodiment, the medical device does not include a sealing material or glue.

In one embodiment, water tight sealing occurred immediately after insertion.

In one embodiment, the plug has a size that is larger than the opening.

In one embodiment, the plug is made of rapidly swelling material.

In one embodiment, the plug comprises one or more hook-like features.

In another embodiment, the present invention provides a method for filling an unwanted or artificially-created space or cavity, or for closing an unwanted or artificially-created opening inside the body of a subject, wherein the method comprises: delivering a filling device to an unwanted or artificially-created space or cavity inside the body of a subject, wherein the filling device is adapted to take the shape that can substantially fill the unwanted or artificially-created space or cavity, or can substantially close the unwanted or artificially-created opening, wherein the filling device is preferably made of biocompatible material. In one embodiment, the method includes a pressurized delivery of a plug larger than the opening.

In one embodiment, the unwanted or artificially-created space, cavity, or opening is created by puncturing a site within the body of a subject, such as during injection of therapeutics into the body.

In another embodiment, the present invention provides a method for preventing leakage of an injected therapeutic agent from a target site of injection within the body of a subject, wherein the method comprises:

injecting a composition comprising a therapeutic agent, and optionally, a pharmaceutically-acceptable carrier, into a target site of the body, wherein the injection creates an unwanted or artificially-created space or cavity inside the body; and delivering a filling device to the unwanted or artificially-created space or cavity, wherein the filling device is adapted to take the shape that can substantially fill the unwanted or artificially-created space or cavity, or can substantially close the unwanted or artificially-created opening, wherein the filling device is preferably made of biocompatible material.

In one embodiment, the medical apparatus of the present invention is used in the course of delivery (e.g., injection) of a therapeutic agent into a target site within the body of a subject, wherein the filling device can be used to substantially fill a space or cavity (or substantially close an opening) created by the delivery of the therapeutic agent, thereby reducing or preventing the leakage of substances (such as the therapeutic agent, bodily fluid, or air/gas substance) into a non-target site within the body of the subject. In one embodiment, the medical apparatus of the present invention reduces or prevents leakage of intra-discal injection of stem cells into nucleus pulposus of an intervertebral disc during cell therapy by delivering the filling device (e.g., annulus plug) into the internal space or cavity created by the intra-discal injection. In another embodiment, the filling device of the present invention is delivered during or after the injection of therapeutic agents including, but not limited to, cell suspension, drugs, growth factors, into a target tissue or organ of interest including, but not limited to, an intervertebral disc (IVD), bone, heart, gut, bladder, and joint. In one embodiment, the present invention can be used to prevent the leakage of air/gas substances after puncturing an internal bodily space (such as the lung or chest cavity) that contains air/gas substances. In one embodiment, the present invention can also be used for filling an unwanted or artificially-created space or cavity (or closing an unwanted opening) within the body including, but not limited to, abscesses, tumour cavities, tissue cavities after surgical expansion.

FIG. 1(A-I) show an embodiment of the medical apparatus of the present invention as well as an embodiment of the method of delivering the annulus plug after injection of cells in intervertebral discs (IVD).

In one embodiment, the invention comprises a filling device (e.g., a plug) that takes the shape of an internal space or cavity, including an internal space or cavity created by an injection needle or a delivery device, or an unwanted space to be filled. In one embodiment, the filling device is an annulus plug having a thin rod-shape. In one embodiment, the filling device (such as an annulus plug) can be delivered via a thin needle (e.g., a syringe needle) and, upon delivery, fills up the space of the injection portal of the syringe needle.

In one embodiment, the filling device (e.g., an annulus plug) comprises or is made of photochemically crosslinked acellular type I collagen matrix. In one embodiment, the filling device (e.g., an annulus plug) comprises or is made of photochemically crosslinked acellular type I collagen matrix with compact fibers meshwork with ~67% of water, simulating that of the native annulus or similar soft tissue, and with a mechanical property that can endure physiological mechanical demand of IVD (such as mechanical loadings applied during a chronic push-out test).

In another embodiment, the filling device (e.g., an annulus plug) comprises or is made of acellular photochemically crosslinked material comprising, consisting essentially of, or consisting of collagen and glycosaminoglycan (GAG) composite. In one embodiment, the filling device (e.g., an annulus plug) comprises or is made of acellular photochemically crosslinked material comprising, consisting essentially of or consisting of collagen and glycosaminoglycan (GAG) composite that has a high glycosaminoglycans (GAG) to hydroxyproline (HYP) (a marker of collagen) ratio that simulates the extracellular matrix composition of the annulus fibrosus.

In one embodiment, the filling device comprises, or is made of photochemically crosslinked material comprising a component selected the group consisting of collagen (e.g., collagen type I, II, III or mixtures thereof), gelatin, proteoglycan, hyaluronic acid, elastin, and mixtures thereof.

In an embodiment, the filling device comprises, or is made of biocompatible material that does not elicit adverse immunogenicity. Biocompatible materials useful for making the filling device include, but are not limited to matrigel, hydrogel, collagen, alginate, collagen-glycosaminoglycan co-precipitates, poly(glycolide) (PGA), poly(L-lactide) (PLA), poly(lactide-co-glycolide) (PLGA), and polyethylene glycol (PEG). In one embodiment, the filling device comprises or is made of naturally-occurring extracellular matrix type I collagen, which has excellent biocompatibility and negligible immunogenicity.

The filling device of the invention can be fabricated and processed in a way that it matches well with the physicochemical properties of the native tissue surrounding the space or cavity to be filled. In one embodiment, the filling device (e.g., an annulus plug) can withstand mechanical and/or physiological environment to which the tissue is subjected. For example, the plug is fabricated, stabilized and strengthened by techniques including photochemical crosslinking technology disclosed in U.S. Pat. Nos. 7,931,918 and 7,393,437, which are hereby incorporated by reference in their entireties. In one embodiment, the photochemically crosslinked plug can withstand physiological loading of the intervertebral disc.

In one embodiment, the medical apparatus comprises a delivery device capable of delivering a therapeutic agent (including but not limited to, fluid-containing substances, cell suspensions, drugs, growth factors and small molecules) and optionally, carrier materials and/or hydrogels, followed by the delivery of the filling device of the present invention to block a space or cavity (such as an injection portal) created by the delivery of the therapeutic agent. In one embodiment, mesenchymal stem cell suspension is injected intra-discally through an injection needle, followed by clamping of the injection needle and subsequent delivery of a photochemically crosslinked annulus plug through the injection needle. In one embodiment, the delivery device of the present invention can position the filling device (e.g., annulus plug) in appropriate location in the internal space or cavity to be filled (e.g., annulus).

In one embodiment, the positioning of the filling device comprises measuring the dimension of the filling device. In one embodiment, the medical apparatus comprises a plunger for pushing the filling device (e.g., a plug) through the delivery device (e.g., a needle) at an appropriate position. Such marker serves as a stop-sign during the insertion or delivery of the filling device (e.g., a plug). In one embodiment, a sticker label is placed on an appropriate position of the plunger before pushing the filling device (e.g., an annulus plug) through the needle during intra-discal delivery of stem cells and the filling device (e.g., an annulus plug).

In one embodiment, the medical apparatus comprises a biocompatible adhesive for sealing the injection site while removing the delivery device after inserting the filling device (e.g., a plug) into position. The sealing reduces or prevents immediate leakage before the filling device (e.g., the plug) is fully swollen to take its shape. In one embodiment, fibrin glue or histoacryl glue can be applied to the surface of the annulus at the injection site, while removing the whole delivery device after positioning the annulus plug. This allows immediate blockage of the injection portal to prevent leakage and provides sufficient time for the plug to swell to enough volume for better and long term blockage.

The filling device (e.g., a plug) is delivered in dehydrated state. Upon contact with the remnant solution of the injected cell suspension or hydrogel or moist host tissue, the filling device (e.g., a plug) rapidly swells or is expanded to a volume that substantially fills up the injection portal or cavity to be filled and press-fits the injection portal or the cavity, thereby reducing or blocking the leakage or passage of the injected substances. In one embodiment, the filling device (e.g., an annulus plug) immediately swells and may swell up to double or triple or more of its original volume to fill up the space to be filled. In one embodiment, after delivery of the filling device to the internal space or cavity to be filled, the filling device expands its volume and swells to fill the internal space or cavity within a time period of 3 seconds to 3 months, or any period there between, including but not limited to, 5 seconds, 30 seconds, 1 minute, 2 minutes, 3 minutes, 5 minutes, 10 minutes, 1 hour, 1 day, or 1 month. The dimension of the filling device (e.g., a plug) can be specifically designed for injection needle of any Gauge, such as for example, 21G, 25G, and 27G.

In one embodiment, the filling device (e.g., a plug) can withstand physiological and/or mechanical demand. In one embodiment, the filling device (e.g., a plug) has sufficient mechanical properties that make it survive physiologically relevant loading or challenges such that leakage of the extrinsically introduced substances will not occur even the tissue is subjected to normal physiological loading. In one embodiment, the filling device is an annulus plug inserted to the annulus fibrosus during intra-discal injection of mesenchymal stem cells in degenerative discs, and the annulus plug can survive normal physiological stress of a subject.

The filling device (e.g., an annulus plug) can prevent leakage. In one embodiment, the annulus plug blocks the injection portal created during delivery of stem cells to rabbit nucleus pulposus and can prevent cell leakage in a cell leakage test. In one embodiment, no more than 0.01% of injected MSC-collagen microspheres were leaked out throughout the 7 days of physiological loading in rabbit disc inserted with the annulus plug, while at least 20% of cell-microspheres were leaked out in the control group; this shows that the filling device (e.g., an annulus plug) of the invention has a satisfactory sealing effect.

In one embodiment, the filling device can integrate with host tissue without creating any substantial or material adverse effect. In one embodiment, cells or tissues can grow on the filling device (e.g., an annulus plug) such that the filling device (e.g, a plug) is sealed at cellular and molecular level.

6. EXAMPLES

Following are examples that illustrate embodiments for practicing the invention. These examples should not be construed as limiting. All percentages are by weight and all solvent mixture proportions are by volume unless otherwise noted.

Example 1

Fabrication of Photochemically Crosslinked Collagen Membranes

An aliquot of 250 µl of rattail type I collagen solution (Becton Dickinson) at a final concentration of 4.0 mg/ml was poured into a cylindrical shaped container with a diameter of 17 mm. The container was placed inside an ammonia vapor chamber for one hour for collagen gelation. The resultant gel was briefly rinsed with excessive distilled water. The collagen gel was equilibrated with a rose Bengal solution at concentrations ranging from 1.965 to 982.5 mmol (0.0002%-0.1%) for overnight at room temperature and under regular agitation to study the rose Bengal dosimetry. The dyed gels were irradiated with an Argon laser (Coherent) at 514 nm with a spot size of 16 mm in diameter at a power of 0.2 W for 100 seconds such that the energy fluence was constant at 10 $J/cm^2$. In a separate experiment, the crosslinked gels were equilibrated with a rose Bengal solution at a constant concentration of 9.825 mmol (0.001%) while the gels were irradiated with the same laser spot for a period ranging from 63 seconds to 1000 seconds such that the energy fluence varied from 6.25 to 1000 $J/cm^2$. Control gels were untreated collagen gel without rose Bengal exposure and laser irradiation. All gels were dehydrated by air-drying for 2 days to obtain thin membranes for FTIR analysis.

Example 2

Fourier Transform Infrared Spectroscopy

In order to investigate direct evidence of covalent bonding of photochemical crosslinking in the annulus plugs, Fourier transfer infrared (FTIR) analysis revealing the protein secondary structural modifications and intermolecular bonding of crosslinked collagen, was conducted. In brief, the air-dried collagen membranes were fixed directly onto the sample plate of a FT-IR spectroscopy system (PerkinElmer) and irradiated by infrared light at a range of frequency from 4000 to 500 cm-1 at a data acquisition rate of 2 $cm^{-1}$ per point to obtain a FTIR spectrum. The background absorption was subtracted automatically from the spectra using the default software and the peak absorbance, the corresponding frequency and other spectral features such as absorbance ratios were analyzed.

This work provides direct evidences of dose-dependent covalent bonding formation in photochemically crosslinked collagen, contributing to enhanced physicochemical properties of collagen scaffolds previously demonstrated (Chan & So, 2005; Chan et al., 2007). First, amide I band refers to stretching vibrations of peptide carbonyl groups of amide groups in proteins. In this frequency range, each secondary structural component in collagen would give rise to a unique C=O stretching absorption frequency (Kong & Yu, 2007). The secondary structural component absorption peaks in photochemically crosslinked samples became more resolvable from the main band peak as the dose of either rose Bengal concentration of laser energy fluence increases, indicating increased proportions of these secondary structures after photochemical cross-linking, contributing to the improved physicochemical properties of cross-linked collagen. Second, amide II band refers to NH bending and is strongly coupled to CN stretching vibration of collagen amide groups. Our results showed minor absorption peaks became more distinctive from the main band peak as the dose of either rose Bengal concentration or laser energy fluence increased, similar to the FTIR spectral changes observed in glutaraldehyde cross-linked hydroxyapatite/collagen nanocomposite (Chang & Tanaka, 2002), suggesting that the nature or even positions of photochemical crosslinking share similarities with that of chemical cross-linking process. Third, amide III band refers to CN stretching and NH bending from the amide linkages, and is associated with triple helical structure of collagen. Our results showed dose dependent spectral changes similar to that chemically crosslinked (Chang & Tanaka, 2002).

FIG. 2 showed the FTIR spectra of collagen samples.

Example 3

Fabrication of Annulus Plug

An aliquot of 1 ml of acid soluble rattail type I collagen (Becton Dickinson) at 4 mg/ml was poured into a cylindrical-shaped container and was placed in an alkaline vapor chamber containing ammonium hydroxide to initiate the gelation process for 1 hour. After a brief rinse in distilled water, the cylindrical collagen gel was equilibrated with rose Bengal solution at a concentration of 9.825 mmol (0.001%) for overnight at room temperature and under constant agitation. Photochemical cross-linking was carried out by irradiating the gel with an Argon laser (Coherent) at 514 nm at 0.2 W for 100 seconds to achieve a laser energy fluence of 12.5 $J/cm^2$. After brief rinsing in distilled water, the crosslinked collagen gel was then shaped into thin needles with length around 5-7 mm and diameter less than 0.5 mm by controlled dehydration until constant mass was achieved. In brief, the crosslinked collagen cylinder was "hanging" on the ceiling of a desiccator via piles of kimwipes. By gravity, the weight of the cylinder would make it elongate along the vertical direction while dehydrate in the radical direction.

In one embodiment, 1 ml of collagen solution can fabricate a long 30-35 mm plug after dehydration.

In one embodiment, 5 plugs can be made from 1 ml of material.

Example 4

Physical Characterization of Annulus Plug

Dimension of a total of 34 annulus plugs were measured by a vernier caliper (Mitutoyo). Since the diameter of the plugs is important for intra-needle delivery, its distribution was analyzed. Swelling properties of annulus plugs were also important because the dimension of the fully swollen or hydrated plugs should match well with that of the internal diameter of the syringe needle during delivery. To characterize the swelling property of the plug, eight air-dried collage plugs had their dry weight ($W_g$) measured and recorded. These samples were then rehydrated in 1×PBS in two four-well plates (Nunclon) at room temperature with constant agitation. The wet weight ($W_w$) of each sample after removing surface water was recorded at intervals (from 0.5 to 168 hours) to continuously track the swelling status of the plug. Swelling ratio for each collagen plug was calculated by the below equation and plotted against time:

$$\text{Swelling ratio} = (W_w - W_g)/W_g$$

FIGS. 3(A-E) show the physical and ultrastructural characterization of the photochemically crosslinked annulus plug. The photochemically cross-linked collagen plug after fabrication was pink in color (not shown) due to the presence of photosensitizer. SEM analysis of the plug was shown in FIGS. 3B-C. The surface of the plug was largely smooth but "wrinkles" with sub-micron roughness were observed under SEM (FIG. 3B). Densely packed fibrous meshwork was found at the cross-section views of the annulus plug (FIG. 3C). The size distribution of annulus plugs fabricated was normally distributed with a mean diameter of 0.26 mm and a SD of 0.03 mm (FIG. 3D) while the length of the plug ranged from 6 to 7 mm. The plug could be easily delivered through a 21G Hamilton syringe needle, which has an internal diameter of 0.51 mm. The swelling ratio of collagen plug was plotted against time in FIG. 3E. The swelling ratio rose rapidly within the initial 2-3 hours and level off in around 24 hours with a value of ~2 that means the original plug swelled by a factor of 2 and reaches a weight of three times of its initial weight.

Example 5

Delivery and Placement of Annulus Plug

To facilitate delivery of cells and annulus plug in one step, a custom-made syringe needle modified from a Hamilton 21G needle used. In brief, the stainless steel part of the needle was cut apart and then reconnected by a polyethylene tubing. After injecting cell suspensions, the tubing was clamped to isolate the pressure between the two ends of the needle to allow pull-out of the needle from one end for insertion of the plug without disturbing the cell suspension injected. After inserting the plug into the 21G needle and then inserting the needle into the plastic tubing, the tubing was unclamped to allow pushing and placement of the plug into the annulus. Immediately after slowly pulling out of the needle, histoacryl glue (TissueSeal) was applied at the injection site to temporarily seal the wound. Successful placement of the plug was assessed by the presence of distinct pink color of the plug at the insertion site during in vivo study. While for the ex vivo leakage and mechanical push-out tests, successful placement of the plug was also confirmed by the presence of the plugs inside the annulus after cross-sectional dissection of the disc.

FIG. 4A showed the gross appearance of AF plug and the modified Hamilton syringe needle for delivery of both the cell-microspheres and the annulus plug. Successful placement of the annulus plug into the disc after cell delivery was crucial. FIG. 4B showed the schematic diagram of delivering the annulus plug into the disc via the custom-made needle using the plunger of the syringe. Among seven trials of ex vivo placement tests, five was successful. FIGS. 4C-E showed successful placements of annulus plugs into rabbit discs during ex vivo tests. The positioning of the plug inside the disc varied among the successful trials. Some showed appropriate positioning at the annulus touching a bit at the NP region (FIG. 4C) while in some cases, the plugs were too long and therefore bended (FIG. 4D) and extending into the NP (FIG. 4E). Application of glue immediately after delivery of the annulus plug was crucial to successful placement of plug because it takes 2-3 hours for the plugs to swell to its full volume to press-fit the injection portal.

The current delivery method solved most of the problems encountered during delivery of both cells and plug, including the major problem of pressure difference between the disc cavity and the atmosphere as well as other technical, operational and cost problems. This delivery method successfully held the intra-discal pressure in a simple way for surgeons to operate and introduce extrinsic therapeutic agents, cells and materials. In addition, the transparent tubing used to connect the truncated syringe needle allows the operator to monitor success delivery of the plug. However, one limitation is that the plug could possibly be stuck at the disconnected part of the needle if the plug bends and the needle parts misalign, making the injection procedure technically demanding. With the current design and continuous improvement of the technical skills of the operators, around 70% success rate on plug placement in first attempt (100% in at most 3 attempts) could be achieved. Further improvement of the design and proper training are expected to further improve the successful rate in single attempt, which is essential for surgical management. As demonstrated, the position of successfully placed plugs in the disc cavity was not always ideal. This is largely due to the mismatch between the length of the plug and the depth to which the plug was inserted. This mismatch could possibly be improved by a more accurate and careful control of the extent to which the plug was pushed into the injection portal. Length of the plug could also be customized according to the disc size to prevent the use of longer plug in smaller disc. Ex vivo practice should be given to operators or surgeons to maximize placement success rate.

Example 6

Isolation and Culture of Mesenchymal Stem Cells in Rabbits

Mesenchymal stem cells were prepared as previous described (Chan et al., 2007). All protocols involving animals were approved by the institutional ethical committee. New Zealand White rabbits of 3 months old were used. Approximately 5 ml of bone marrow was aspirated from the tibia upon anesthesia. After Ficolle-Hypaque gradient separation, mononuclear cells at the interface were collected and cultured in Dulbecco's modified Eagle's medium (DMEM) containing 10% fetal bovine serum (FBS) and antibiotics. The medium was refreshed 10 days post-seeding and replenished every 2 days thereafter. When approaching confluence, cells were trypsinized for subcultures in full medium consisting of Dulbecco's modified Eagle's medium-high glucose (DMEM-HG), 10% FBS, 100 U/ml penicillin, 100 mg/ml streptomycin, 1.875 mg/ml sodium hydrogen carbonate ($NaHCO_3$), 0.02 M HEPES, and 0.29 mg/ml L-glutamine. Live cells were separated from dead cells by adherence selection for 24 h and maintained with medium replenishment every 3 days. Passages 2 were used for subsequent microencapsulation.

Example 7

Ex Vivo Leakage Test

In order to quantify the amount of leaked materials, the collagen materials used for microencapsulation of MSCs were labeled by using Alexa Fluor® 488 (Becton Dickinson), at a mass ratio of 1 to 5 (labeled collagen to unmodified collagen), before microencapsulating autologous rabbit MSCs as previously described (Chan et al., 2007). The fluorescent labeled collagen was neutralized with 1N NaOH solution before mixing with rabbit MSC suspension in culture medium to obtain a mixture with a final collagen concentration of 2 mg/ml and a final cell density of 1.25E5 cells/ml. Droplets of 2 µl were dispensed onto a Petri dish covered with a piece of parafilm, which was disinfected previously by UV irradiation. Around 1000 microspheres, each with 250 cells were formed after incubation at 37° C. for around 45 minutes for gelation. The microspheres were flushed into and cultured in culture medium for three days before injection. All procedures for animal experimentation were ethically approved by the institution and followed strictly the regulations. Intervertebral discs harvested from the thoraco-lumbar segment of 9 New Zealand White rabbits were firstly aspirated by a 20 ml syringe with a 21G needle (Terumo) to remove the NP. The custom-made delivery device was fitted onto a Hamilton syringe with a capacity of 25 µl, which was pre-filled with ~900 fluorescence labeled MSC-collagen microspheres, occupying a total of ~20 µl. The MSC-collagen microspheres and a photochemically crosslinked collagen annulus plug were delivered to each disc and sealed as previously described in Section 2.5. The disc was then fitted onto a bioreactor for chronic compression loading for 7 days as described in subsequent section to simulate physiological relevant loading in rabbits. Culture medium inside the bioreactor chamber was collected at 1, 4 and 7 days during compression loading and pooled before measurement of fluorescent signals. In the mean time, at the end of 7 days compression, the disc was dissected to retrieve the retained MSC-collagen microspheres inside the nucleus pulposus for measurement of fluorescent signals. In brief, the samples were centrifuged to pellet any solid materials before enzymatically digested by collagenase (C9891-25MG, Sigma) at a volume ratio of 1:1 at 37° C. for 4-8 hours to obtain the sample lysate. Fluorescent signals of 200 µl of the sample lyzates were measured at a peak emission wavelength at 519 nm using a microplate reader (Safire, Tecan). A fluorescence internal standard curve was constructed to calibrate for the fluorescent signals detected in samples of the leakage test. In brief, five groups of microspheres ranging from 25 to 400 microspheres were prepared in addition to those used for injection during the leakage test. Samples were diluted to a concentration within the linear range of the calibration curve.

Figure 6A:
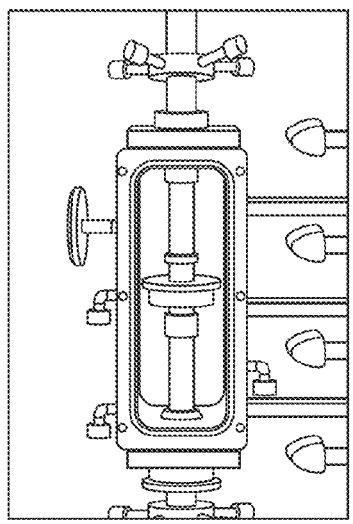
Figure 6B:
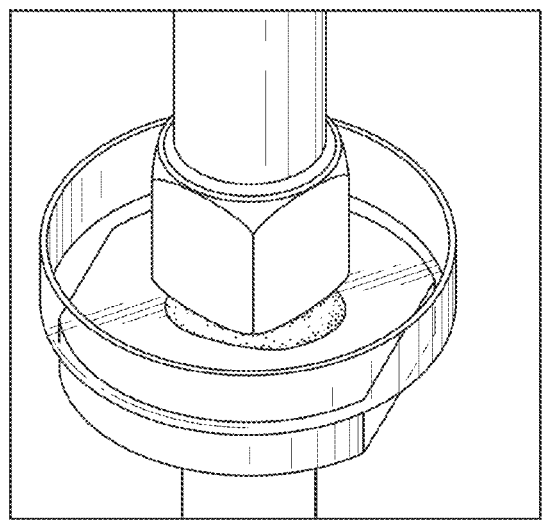
Figure 6C:
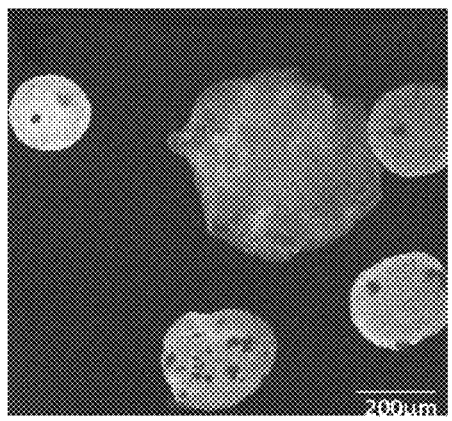
Figure 6D:
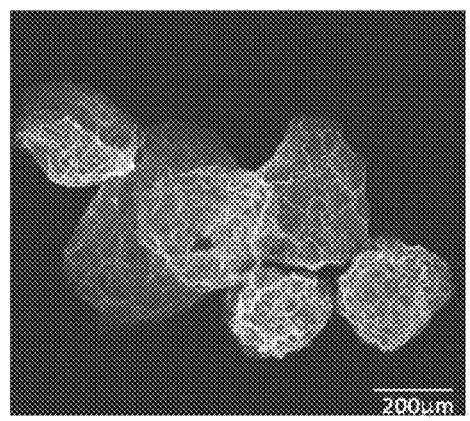
Figure 6E:
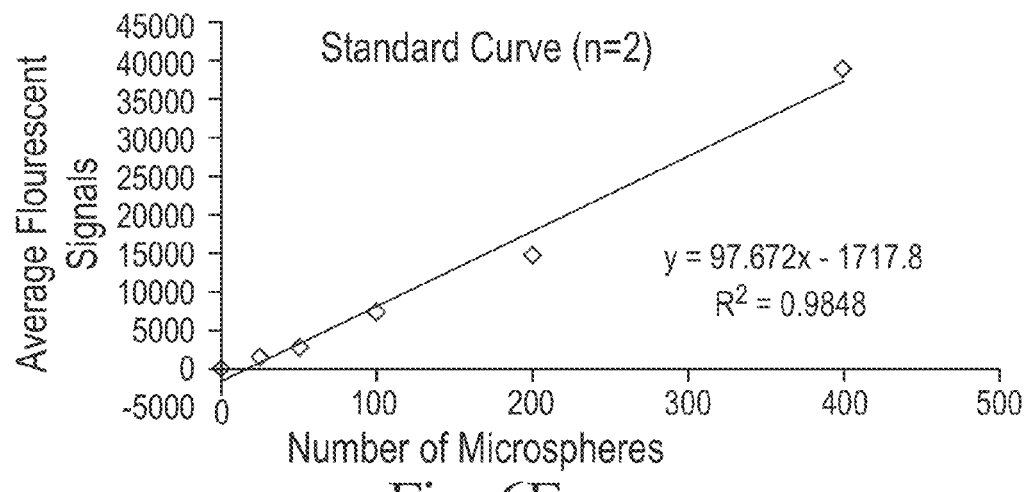

FIGS. 6A-B showed IVDs injected with MSC-collagen microspheres undergoing 7 days of the compression loading regime used in the push-out test. FIG. 6C shows the confocal microscopy images of the Alexa488-labelled collagen microspheres encapsulating MSCs before injection. FIG. 6D shows the labeled microspheres retrieved from the IVD after 7 days of compression loading, although "wrinkled", these microspheres were still intact and the fluorescent signals were retained. Fluorescence signal of the lysate prepared from a series of known numbers of Alex488-labelled collagen microspheres entrapping MSCs showed a linear relationship with a high regression coefficient of 0.992, with a $R^2$ of 0.985 (FIG. 6E), suggesting that measuring the fluorescent signal is a good prediction of the number of labeled microspheres.

Figure 6F:
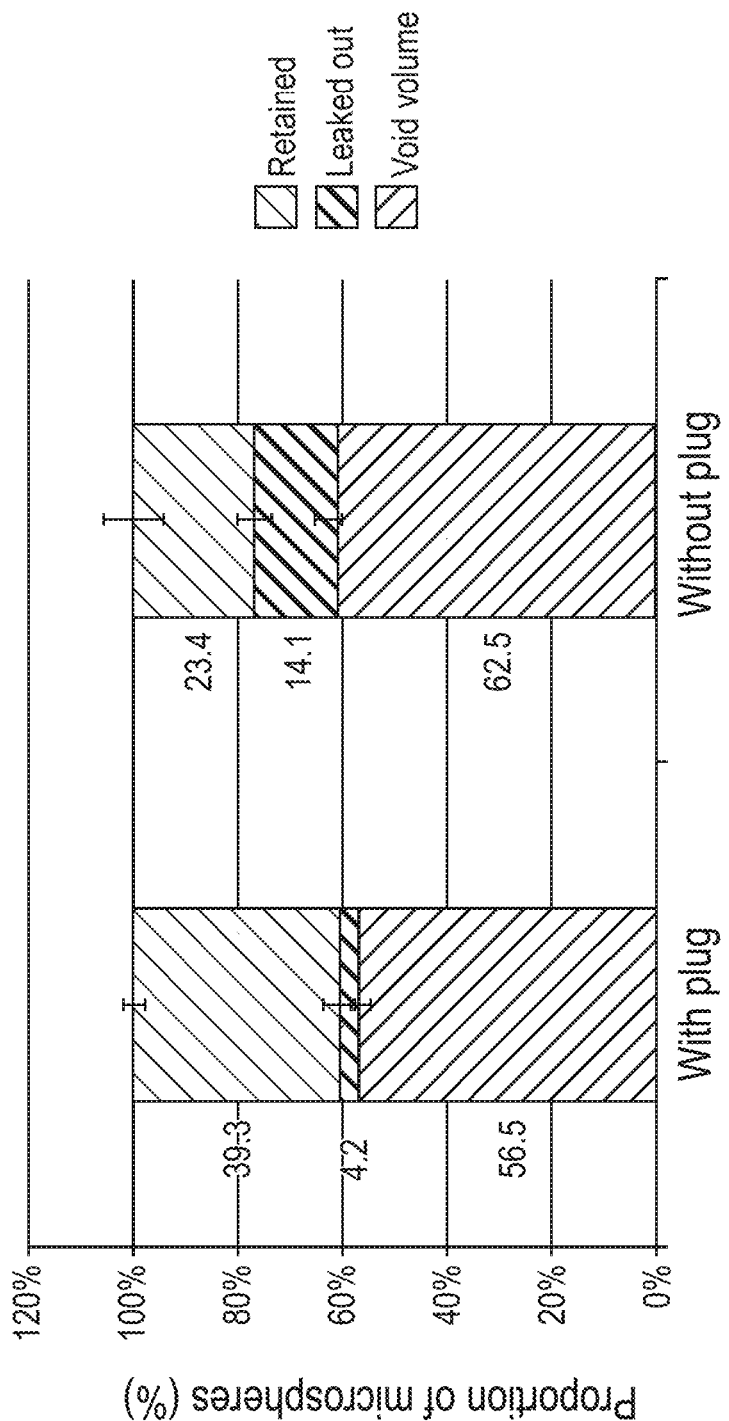

FIG. 6F showed the mean percentage of labeled microspheres trapped inside the void volume of the syringe on day 0, leaked out from the discs into the culture medium during 7 days of compression and retained inside the discs in the NP cavity after 7 days of compression. Same number of microspheres was injected in both with and without plug groups. Upon delivery, there were on average 57% of microspheres were entrapped in the void volume of the syringe needle in the group with AF plug while there were 63% of microspheres entrapped in the void volume of the group without AF plug. Two sample t-test showed that there was significant difference between these two groups ($p=0.033$). With the annulus plug, there were only ~4% of injected microspheres leaked out from the disc specimens into the culture medium during 7 days of compression while there was 14% found in the control group without the plug. Two sample t-test showed that the difference between the annulus plug group and the control group was statistically significant ($p=0.017$). At the end of 7 days compression, ~40% of labeled microspheres were able to be retrieved from the NP cavity, i.e. retained inside the disc, in the group with AF plug insertion while only ~23% of microspheres were retrieved in the control group without the plug. Two sample t-test showed that the difference between the annulus plug group and the control group without the annulus plug was statistically significant ($p=0.01$).

Example 8

Compression Loading Regime for Ex Vivo Leakage Test and Push-Out Mechnical Test Diurnal dynamic loading at physiological frequency (Wang et al., 2007; Ching et al., 2004; Masuoka et al., 2007) is essential to maintain disc health and function (MacLean et al., 2005; MacLean et al., 2004). A seven-day physiological compression loading protocol taking reference from a previous study (Illien-Junger et al., 2010) was developed to evaluate the mechanical durability of the annulus plug. In brief, the disc was placed into a beaker filled with 20 ml of rabbit-MSC culture medium and was placed into the compression loading chamber of a bioreactor (5210 BioDynamic System, Bose) for loading at 37° C., 5% $CO_2$, and ambient $O_2$. The diurnal loading involving both cyclic and static loading consisted of an active phase and a resting phase, both of which mimic the physiological behavior of a rabbit. During the sixteen-hour active phase, cyclic sinusoidal load varies between 0.4 to 0.8 MPa, i.e. 0.2 MPa above and below a mean stress of 0.6 MPa at a frequency of 0.2 Hz. During the eight-hour resting phase, a 0.2 MPa static loading was applied. At the end of 7 days' loading period, a total of 40320 cycles were carried out. The disc specimens were physically examined to determine whether the plug was pushed out or not, before dissecting at the cross-sections to retrieve the microspheres retained in the NP region for fluorescence measurement.

Example 9

Torsion Loading Regime for Ex Vivo Push-Out Test

Another seven-day torsion loading was developed to evaluate the mechanical durability of the annulus plug. On the day before testing, the disc was placed and adhered between two custom-made platens using two component epoxy paste adhesive (Araldite® AW2104/Hardener HW 2934, HUNTSMAN) and was placed into the loading chamber of a bioreactor (5115 BioDynamic System, Bose) for loading at 37° C., 5% $CO_2$, and ambient $O_2$ the day after. The protocol includes a cyclic torsion loading active phase and a resting phase. During the sixteen-hour active phase, cyclic sinusoidal angular displacement varies between 0 to 25° anti-clockwise at a frequency of 0.2 Hz. During the eight-hour resting phase, specimen was kept at 0°. At the end of 7 days' loading period, a total of 40320 cycles were carried out. The disc specimens were physically examined to determine whether the plug was pushed out or not.

FIGS. 5(A-I) showed the results of compression and torsion push-out tests of the annulus plugs. Annulus plugs delivered into rabbit discs were intact before (FIG. 5A), during (FIGS. 5B-C) and after (FIG. 5D) compression and torsion (FIG. 5E) push-out tests. FIG. 5F showed the loading pattern of compressive pull-out test while FIG. 5G showed the loading pattern of torsion pull-out test. All samples survived the chronic compression loading regime, which consists of an active cyclic compression loading phase of 16 hours with a mean stress of 0.6 MPa, roughly corresponding to ~45N, the body weight of a rabbit, at a 0.2 Hz frequency, and a passive static resting loading phase with a stress of 0.2 MPa for 8 hours. Meanwhile, upon torsion loading of 25°, all annulus plugs remained intact after 7 days of push-out test (FIG. 5E). FIGS. 5H & I showed the parameters used for the compressive and the torsion loading push-out tests, respectively.

In the current study, inserted annulus plugs survived more than 40,000 cycles of physiologically relevant compression or torsion loading in the ex vivo push-out tests. This compares favorably with other cyclic loading fatigue tests used to evaluate glues and suturing methods (Heuer et al., 2008) for annulus sealing (Cauthen, 2003; Ferree, 2002; Lambrechet et al., 2005) during insertion of nucleus prostheses ((Heuer et al., 2008; Di Martino et al., 2005) where resistance to loading only sustained up to a range from 3400 to 16,900 cycles. Although direct comparison cannot made between these studies because the animal model, the type of closure devices, the loading conditions and the mechanical testing devices are different, the number of loading cycles survived by the annulus plug in the push-out tests does represent a long term fatigue test. Nevertheless, the annulus plugs in most cases could not be retrieved one month post-delivery, leaving the injection portal visible upon histology examination. This suggests that the plug might be extruded out upon prolonged or extreme loading. One possible reason of this phenomenon is that the plug is completely degraded but this is very unlikely because our previous study showed that photochemically crosslinked membranes were intact after 6 months of subcutaneous implantation (Chan et al., 2007). A second possibility is that the plug was retained for a certain period of time and then extruded out in long term. This is possible because ex vivo study demonstrated that the plug was well retained for at least 7 days with physiological loading and that is sufficient to block the cell leakage and reduce osteophyte formation as shown in the leakage test and the animal study. This should be owing to the slow integration between the plug and the surrounding host annulus tissue. Further improvements such as coating the plug with growth factors or chemo-attractants stimulating cellular penetration and proliferating to enhance integration at cellular level are necessary.

Example 10

Pilot In Vivo Efficacy Test for the Annulus Plug

Nine rabbits were used in the pilot in vivo study. Two months after bone marrow aspiration, when the rabbits become skeletally mature, disc degeneration was induced using a needle aspiration technique modified from a previous study (Ho et al., 2008). The NP was aspirated by a 20 ml syringe with a 21G needle at one month before injection of MSC-collagen microspheres. An aliquot of ~900 MSC-collagen microspheres were injected by the 25 ul syringe with the custom-made 21G needle before delivering the annulus plug. In the control group, MSC-collagen microspheres were injected without the placement of the annulus plug. Histoacryl glue was applied to both groups to prevent immediate leakage and to buy time for the plug to swell to press fit the injection portal.

For the pilot in vivo study, annulus plugs were successfully placed in the desired positions with at most three attempts for all nine cases. FIGS. 7(A-G) show the radiographic evaluation of disc height, hydration index and osteophyte formation of degenerative discs repaired with MSCs in collagen microspheres with and without the annulus plug. FIG. 7A showed representative x-ray radiographs of the involved discs. FIG. 7B showed the contingency table of the frequency of osteophyte formation based on x-ray radiograph (FIG. 7A) and physical examination of the gross appearance (FIG. 7E) of the involved discs. Using these assessment methods, only 2 discs with injection of MSC-microspheres without annulus plugs were found with osteophytes while no other osteophyte was found. FIG. 7C showed the box plots of mean MRI hydration index of different groups. Injecting MSC-microsphere followed by annulus plug did not result in changes in hydration index as compared to those without annulus plug ($p=0.809$) while both groups showed significantly lower values than the uninjured control group ($p<0.001$). FIG. 7D showed the box plots of the disc height index assessed by x-ray radiographs. Again, injecting MSC-microspheres with annulus plug did not result in significant changes in disc height as compared with that without annulus plugs ($p=1.000$) but both groups showed significant difference from the uninjured controls ($p<0.001$). FIG. 7E showed the gross appearance of involved disc levels while FIG. 7F showed the representative images of microCT volumetric analysis in different groups. Determination of osteophyte formation using microCT volumetric analysis was a lot more sensitive than that by x-ray radiographs as shown by the difference in frequency of osteophyte formation assessed by x-ray radiograph (FIG. 7B) and by microCT volumetric analysis (FIG. 7G), where signs of osteophyte formation were found in all but one uninjured specimen, of the same sets of involved discs. Moreover, microCT analysis also gave quantitative information on volume of osteophyte formed (FIG. 7G). One-way ANOVA showed statistical significant difference in osteophyte volume among different groups ($p<0.001$) while Tukey HSD post-hoc analysis showed that statistically significant differences were found between those with and without annulus plug ($p=0.002$), and between the uninjured control and those without annulus plug ($p<0.001$) but not between the uninjured control and those with annulus plug ($p=0.57$).

Example 11

X-Ray and MRI Analyses

Functional outcomes of disc degeneration including hydration index by MRI and disc height index by x-ray radiography (Supplementary information 1) were monitored. MRI monitoring at pre-injection (time 0) and 1 month post-injection was conducted as previously reported (Ho et al., 2008). Briefly, Sagittal T2-weighted images of lumbar spine were taken using Siemens Magnetom Trio scanner (3T) in Hong Kong Sanatorium & Hospital. Mixtures of different ratio (10:0, 8:2, 6:4, 2:8, and 0:10) of derterium oxide/water in cryotubes were scanned along with each rabbit as internal standard of hydration index. A fish oil capsule (Alaska, Nu-health products Co.) was also scanned together to confirm that the fat suppression sequence was active. Images were viewed using Syngo FastView tools (windowing at W:600 C:280) and serial images that contained signal from T2/T3, T3/T4 and T4/T5 levels were extracted. Three to five slices were analyzed for each disc. Anterior-posterior radiographs of rabbit spine were taken at pre-degeneration (−1), pre-injection (0) and 1 month post-injection using cabinet X-ray system (model 43855a; Faxitron, Ill.) with an exposure time of 18 second and penetration power of 45 kv. DHI of rabbit disc was calculated as previously described (Chujo et al., 2006).

Example 12

Microct Analysis

The change of DHI was expressed as % DHI (post-injection DHI/pre-injection DHI). Osteophyte formation was an important complication of cell-based therapy in disc regeneration (Vadala et al., 2012). In this study, osteophyte formation was assessed by firstly, x-ray radiograph and secondly x-ray computed tomography. At 1 month, rabbits were sacrificed the whole spine was taken out and spinal motion segment in L2-3, L3-4 and L4-5 were isolated for microCT and subsequent histological analyses. Segments were immersed in normal saline solution and X-ray computed tomography (CT) was performed to investigate the presence of osteophyte and to measure the volume of osteophyte. Segments were put in micro CT machine (SkyScan, BRUKER-MICROCT) and data collected were reconstructed and analyzed using Data-Viewer (BRUKER-MICROCT). In brief, all signals in the interverbral disc region between the two flanking vertebrae were regarded as bony osteophyte structure, A window covering all signals between the two vertebrae was assigned and the area covered by these signals was calculated for each segment. The total bone volume was calculated by addition of all segments by the default program.

Insertion of collagen plug into annulus upon intra-discal injection of MSC-collagen microspheres resulted in significantly reduced leakage and increased retention of MSC-collagen microspheres upon 7 days of compression and torsion loading in the ex vivo test. This finding associates well with the effective reduction of osteophyte formation upon x-ray, microCT and histological analyses in vivo. This work suggests that blocking the injection portal using an annulus plug may alleviate the potential safety problem associates with intra-discal delivery of cells and materials, greatly facilitating clinical translation of MSC-based therapy in disc degeneration. Current study shows that microCT analysis presents a more sensitive method than x-ray analysis in detecting and quantifying osteophyte formation. MicroCT analysis can be used to detect signs of osteophyte formation as early as 1 month post-operation, comparing to a previous study reporting osteophyte formation in all specimens using x-ray analysis at 3 months post-operation (Vadala et al., 2012). Micro CT has greatly increased the sensitivity of osteophyte formation in discs because this approach has eliminated superposition and foreshortening of anatomic structures, which lead to poor sensitivity of x-ray radiography in detecting osteophyte in early stage. Quantitative microCT analysis of osteophyte should be included as a standard evaluation of emerging disc regeneration therapies as osteophyte formation is an indicator of leakage of injected cells and materials and hence a common side-effect or complication of ultra-discal delivery of therapeutic agents.

Photochemical crosslinking of collagen is covalent in nature. Employing this technology, an injectable photochemically crosslinked collagen plug with appropriate physical properties was fabricated to block the injection portal upon intra-discal injection of MSC in collagen microcarriers. Ex vivo push out tests demonstrated that the plug survived mechanical loading of physiologically relevant range, and significantly reduced leakage and enhanced intra-discal retention of injected MSCs in collagen microspheres. These results associate well with that of the in vivo study where significant reduction in osteophyte formation upon insertion of the collagen plug was demonstrated as shown from both the quantitative micro-CT volumetric analysis and the qualitative histological examination. Our results further suggest that micro-CT is a more sensitive method than x-ray radiography to evaluate osteophyte formation upon intra-discal injection of therapeutics.

Example 13

Histological and Immunohistochemical Evaluation

Paraffin (10 µm) sections of the IVD in cross-sectional plane were prepared to evaluate the histological and immunohistochemical markers of IVD. Haematoxylin & Eosin (H&E) staining reveals the cell morphology, Alcian blue staining reveals the glycosaminiglycan (GAG)-rich region, Von Kossa staining reveals the calcium deposition in bony region, and immunohistochemistry against collagen type I and type II revealed the phenotypic properties of osteophyte, if any, respectively. For collagen type I and type II, sections were incubated with 0.1% pronase (Sigma) at room temperature for 15 minutes and 0.5% pepsin (Sigma) in 5 mm HCl at 37° C. for 30 min for antigen retrieval respectively. After overnight incubation at 4° C. with mouse monoclonal antibodies against anti-type I collagen (Sigma, Cat. No. C2465) (1:800 in PBS) and anti-type II collagen (Calbiochem, Cat. No. CP18) (1:2000 in PBS) respectively, sections were incubated with anti-mouse immunoglobulin G (Dako, Glostrup, Denmark) (1:200 in PBS) for 30 min at room temperature. The Vectastain ABC kit (Vector Lab Inc., Burlingame, Calif., Cat. No. BA2000) and the DAB substrate system (Dako) were used for color development and hematoxylin (Vector Laboratories) was used as the counterstain.

FIGS. 8(A-O) show the histological and immunohistochemical staining of important disc matrix markers including GAGs, type II collagen and osteophyte markers including von Kossa staining for calcium deposits and Alcian blue staining for GAGs. FIGS. 8F-J showed the intact annulus fibrosus, with strong GAG staining, negative calcium staining, slight positive type I and II collagen immunohistochemistry, respectively. No osteophyte was noted. FIGS. 8A-E showed that the injection portal was still noticeable at 1 month post-operation in IVD with annulus plug insertion. No osteophyte was found. Similar to the uninjured control, disc matrix markers including GAGs (FIG. 8B) and type II collagen (FIG. 8E) were positive. Type I collagen staining was more intensive at the outer annulus (FIG. 8D) and no signs of calcification was noticed (FIG. 8C). FIGS. 8K-O showed that the injection portal still noticeable in disc without annulus plug insertion. Large and calcified (FIG. 8M) osteophyte, positive for GAGs (FIG. 8L) and immunopositive for type I (FIG. 8N) and type II (FIG. 8O) collagen, suggesting its endochondral ossified nature, extending outside the annulus fibrosus around the injection portal was identified.

Example 14

Statistical and Data Analysis

Quantitative data such as FTIR peak values and frequencies, annulus plug dimension and swelling ratio, proportion of labeled MSC-collagen microspheres leaked out and retained, MRI hydration index, x-ray disc height index and microCT osteophyte volume were presented as means with standard deviations unless otherwise stated. Assumption on normality was verified before parametric tests were used. One-way ANOVA with appropriate post-hoc tests were used to reveal the difference among different groups in FTIR peak values, swelling ratio and osteophyte volume. Linear regression analyses were used to reveal the association of FTIR frequency and ratio data with rose Bengal and laser fluence dosimetry. Students' t-tests were used to reveal the difference in microsphere leakage and retention between groups with and without annulus plug. One-way or two-way ANOVA with appropriate post-hoc tests were used to reveal difference among different groups for microCT, MRI and x-ray analyses. SPSS 19.0 was implemented in data analysis and the significance level was set to be 0.05.

Figure 2C:
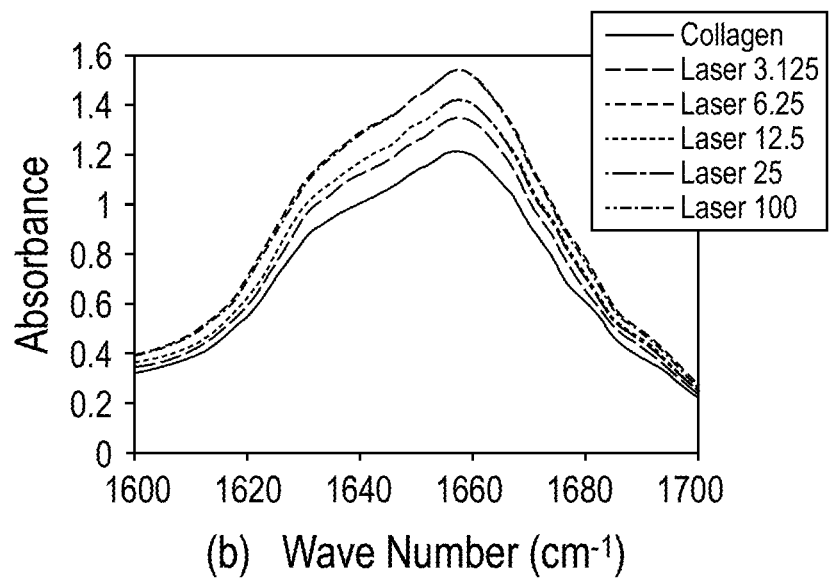
Figure 2D:
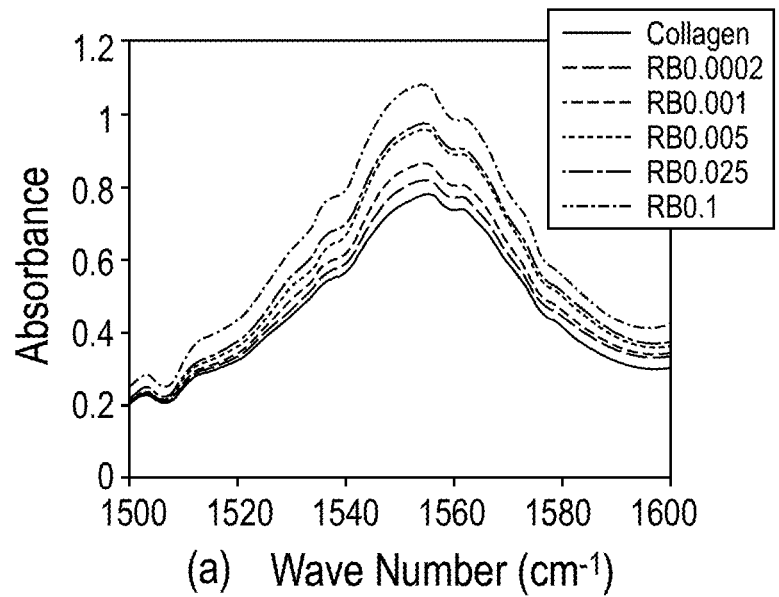
Figure 2E:
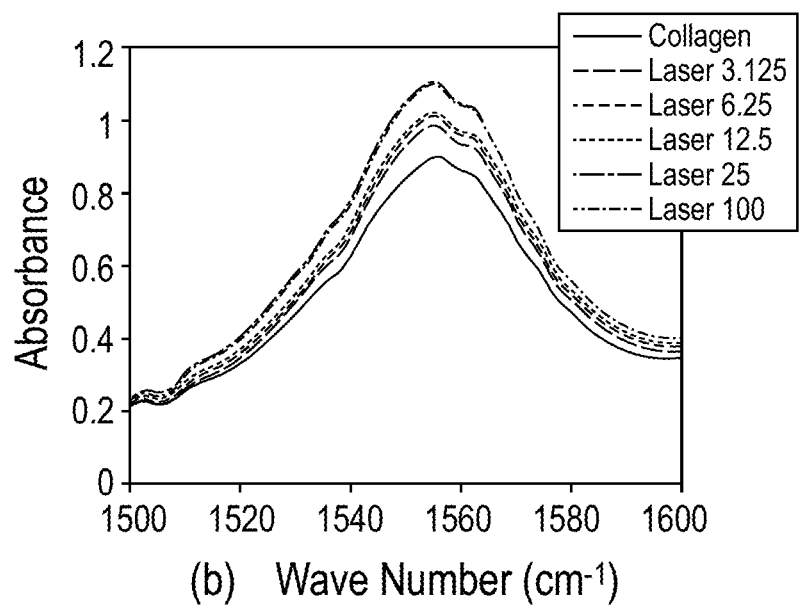
Figure 2F:
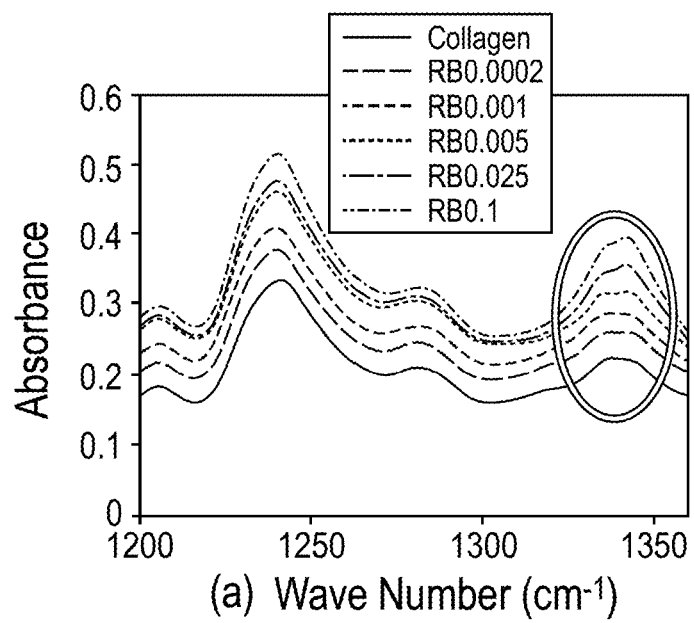
Figure 2G:
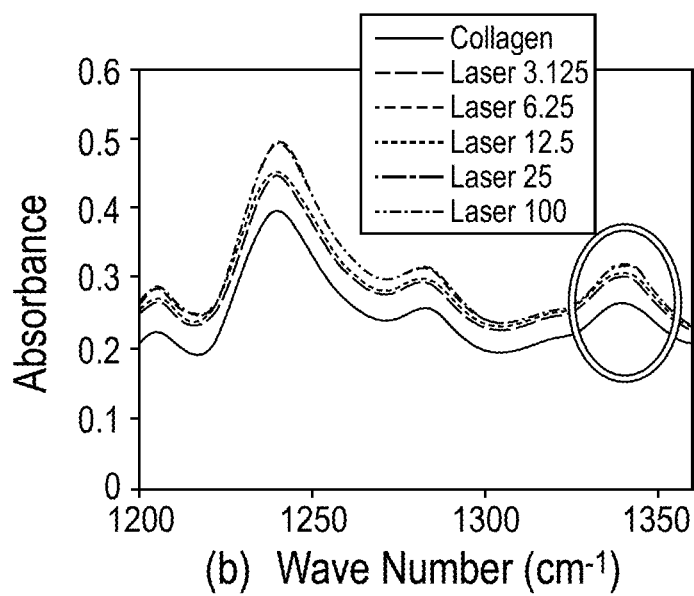
Figure 2H:
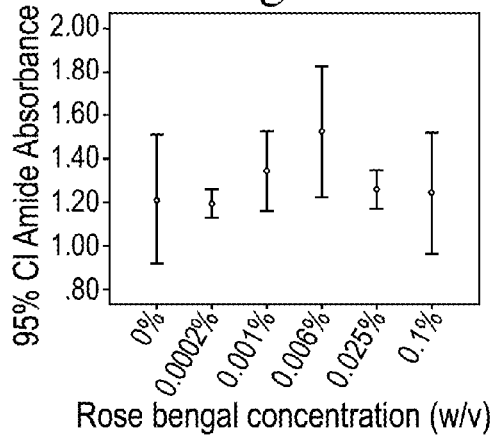
Figure 2I:
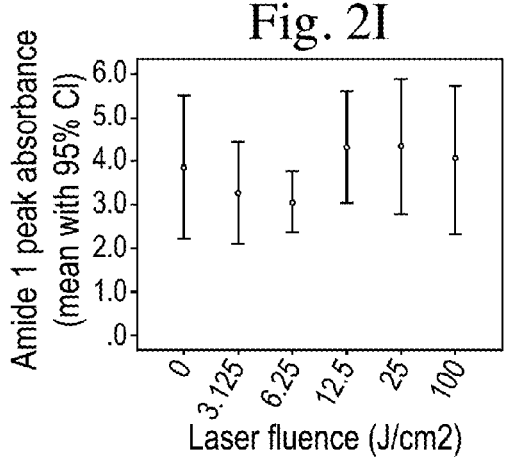
Figure 2J:
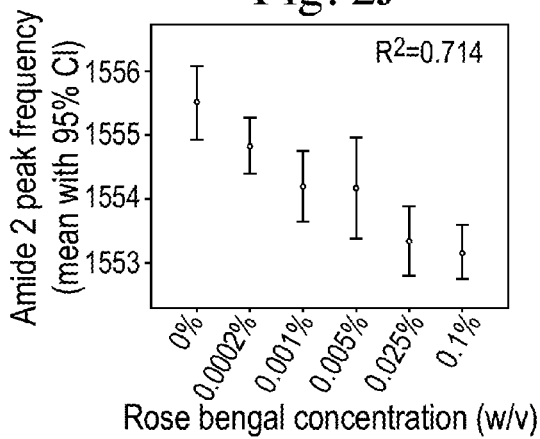
Figure 2K:
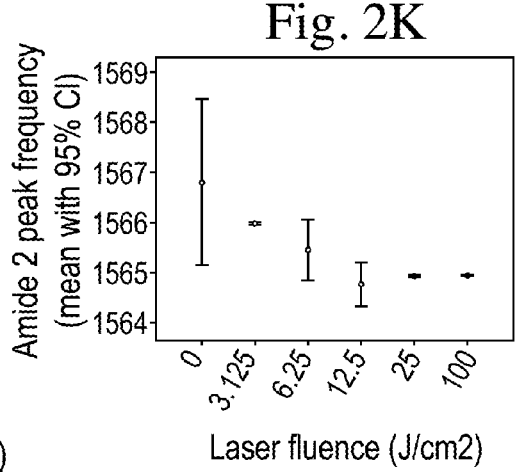
Figure 2L:
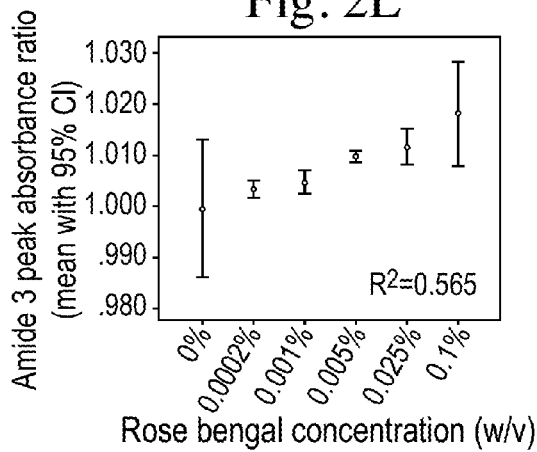
Figure 2M:
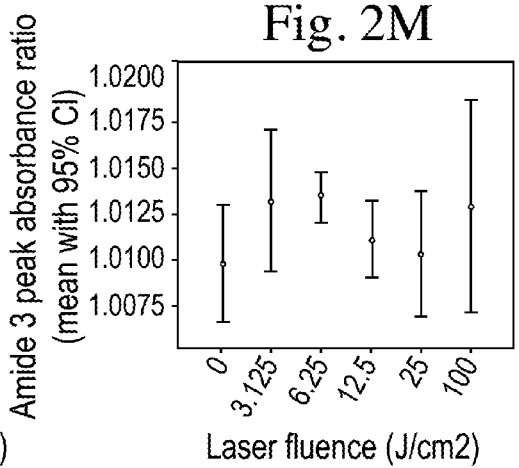
Figure 3A:
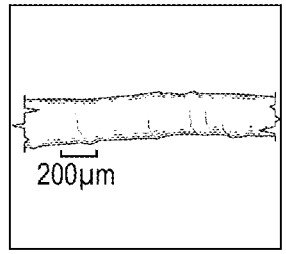
Figure 3B:
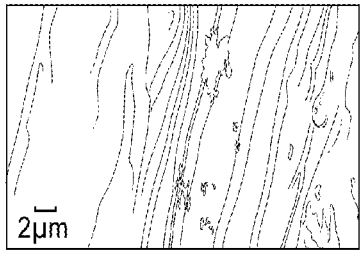
Figure 3C:
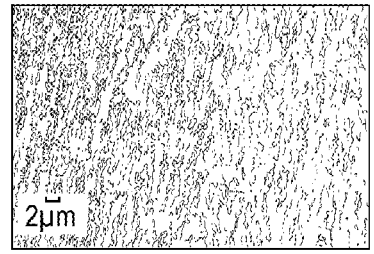
Figure 3D:
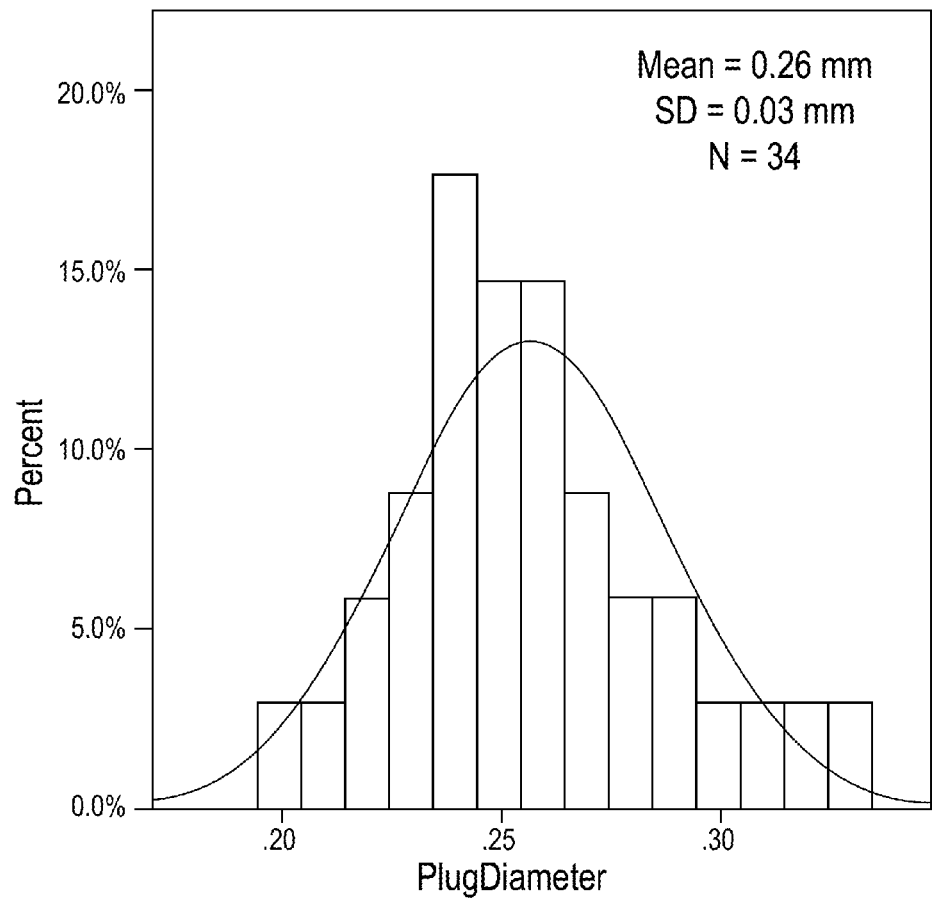
Figure 3E:
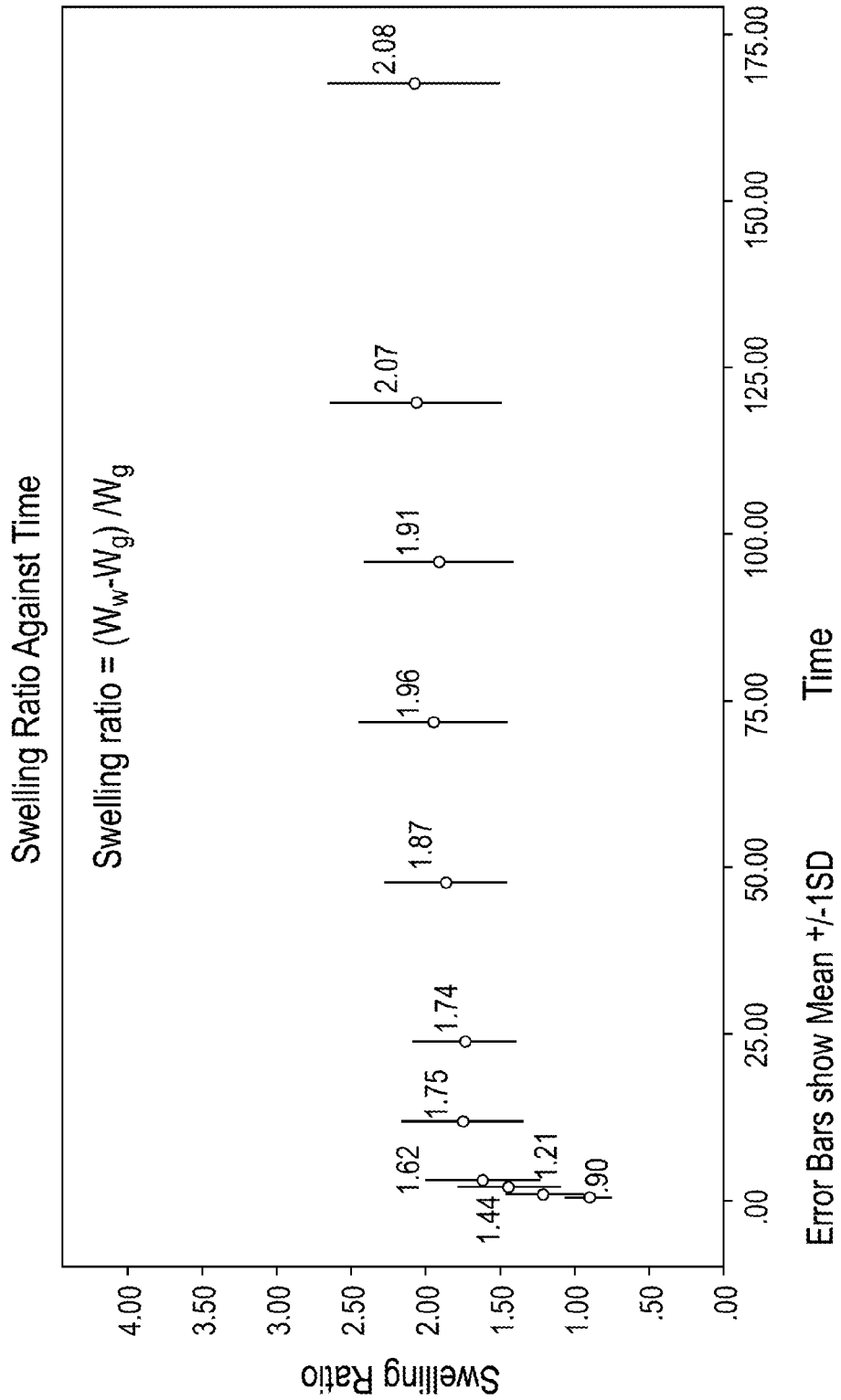
Figure 5A:
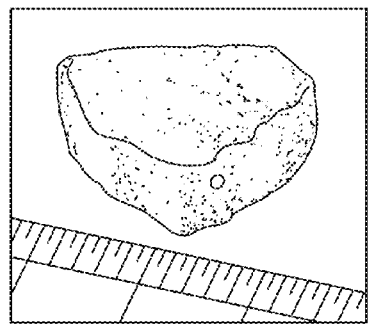
Figure 5B:
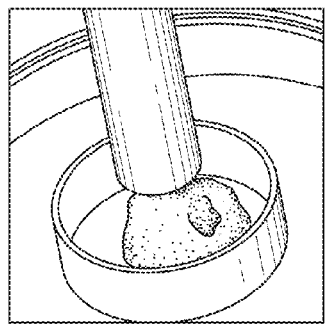
Figure 5C:
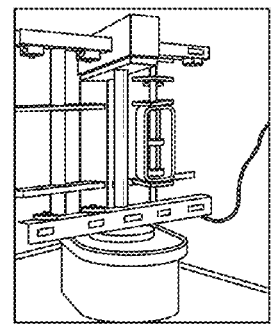
Figure 5D:
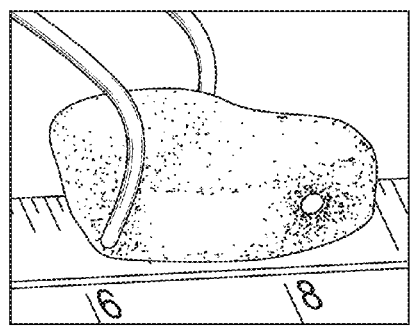
Figure 5E:
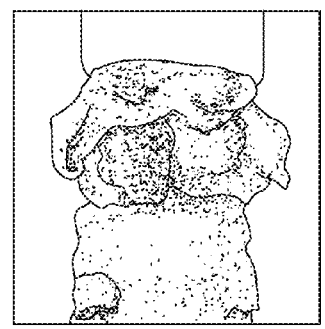
Figure 5F:
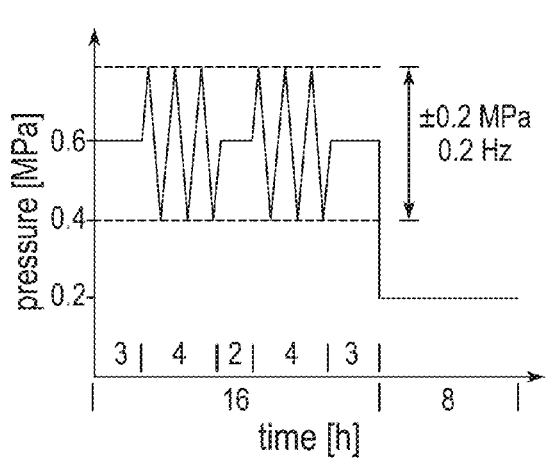
Figure 5G:
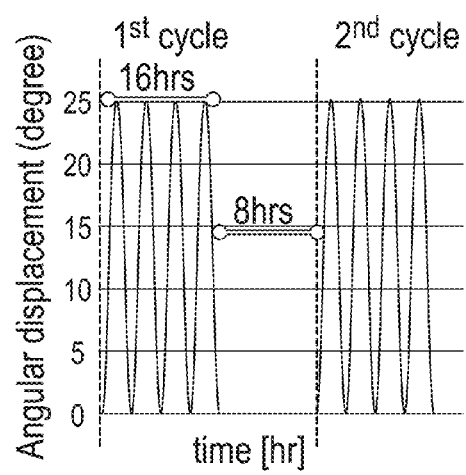

FIG. 2A showed typical wide scan (400-4000 $cm^{-1}$) FTIR spectra of uncrosslinked and photochemically crosslinked collagen samples. There were notable mismatches in both the peak intensity and the peak frequency between the two spectrums at several frequency ranges. Typical amide bands included amide I band peaking at around 1658 $cm^{-1}$, amide II band peaking at 1555 $cm^{-1}$, and amide III band peaking at 1240 $cm^{-1}$. Analysis for individual amide I band spectrum at different rose Bengal concentration and laser fluence were shown in FIGS. 2B-7E. Slight increase in Amide I peak absorbance was observed as the concentration of rose Bengal increased from 0.0002 to 0.005% (w/v) but the values leveled off afterwards (FIGS. 2B&D) and such change was not statistically significant although marginal as shown by one-way ANOVA ($p=0.07$). There was a light increase in Amide I peak absorbance as laser fluence increased from 3.125 J/$cm^2$ but it saturated at 12.5 J/$cm^2$ (FIGS. 2C&E). One-way ANOVA with Bonferroni's post-hoc tests showed no significant difference between the peak absorbances of uncross-linked and photochemically cross-linked collagen at various laser energy fluences ($p=0.359$). There was no notable changes in peak frequency and shape in Amide I region (data not shown). Analysis for individual amide II band spectrum at different rose Bengal concentrations and laser fluences were shown in FIGS. 2F-7I. There was no notable change in peak absorbance in Amide II region (data not shown). However, a significant peak shift towards a lower frequency was observed in Amide II band as the concentration of rose Bengal increased from 0.0002 to 0.1% (w/v) (FIG. 2F) and such change was significant using one-way ANOVA ($p<0.001$) and linear with a $R^2$ of 0.714 (FIG. 2H) using linear regression analysis ($p<0.001$). Amide II peak shift towards lower frequencies was also not noticed as the laser fluence increased from 3.125 to 12.5 J/$cm^2$ and then leveled off (FIGS. 2G&I). One-way ANOVA among different fluence groups showed significant difference ($p<0.001$) while Dunnett T3 post-hoc tests showed that 12.5 J/$cm^2$ group was statistically different from 3.125 J/$cm^2$ group ($p=0.008$) but not other groups (FIG. 2I). Analysis for individual amide III band spectrum at different rose Bengal concentrations and laser fluences were shown in FIGS. 2J-2M. There was no notable change in peak absorbance in Amide III region (data not shown). The spectral shape in this region, as shown by the peak absorbance ratio at 1336 and 1343 $cm^{-1}$ showed increase as the concentration of rose Bengal increased from 0.0002 to 0.1% (w/v) (FIG. 2J) and such changes was significant using one-way ANOVA ($p<0.001$) and linear with a $R^2$ of 0.565 (FIG. 2L) using linear regression analysis ($p<0.001$). This peak absorbance ratio in Amide III band was not obvious as the laser fluence increased from 3.125 to 100 J/$cm^2$ (FIG. 2K). One-way ANOVA among different fluence groups showed no significant difference ($p=0.210$) (FIG. 2M).

CONCLUSION

Mesenchymal stem cells (MSCs) is useful in developing new treatments for intervertebral disc (IVD) degeneration (Sobajima et al., 2008; Zhao et al., 2007; Raj, 2008; Risbud et al., 2004; Vadala et al., 2008). Encouraging results including increased matrix deposition, better maintained disc height and water hydration index and signs of differentiation of MSCs have been demonstrated in mice (Yang et al., 2009), rats (Crevensten et al., 2004), rabbits (Sakai et al., 2003; Sakai et al., 2005; Sakai et al., 2006; Cheung et al., 2005; Miyamoto et al., 2010) and pigs (Henriksson et al., 2009). However, the safety of intra-discally injecting MSCs to treat disc degeneration should be critically evaluated before well-designed clinical trials can be conducted. One long-lasting problem, which might lead to unfavorable results and sub-optimal efficacy of MSC-based therapy, is cell leakage.

IVD contains a central soft gel-like core called nucleus pulposus (NP), which is contained in a multi-lamellae collagenous annulus fibrosus (AF). IVD is sandwiched between two units with cartilaginous endplate connected to adjacent vertebrae. NP is rich in proteoglycans and thus highly water absorbing, generating a high swelling pressure against the AF lamellae. This contributes to a high intra-discal pressure, making injection of any material into healthy disc difficult (Roberts et al., 2008). Puncturing through the annulus into the cavity containing NP is necessary during injection but the high intra-discal pressure would extrude the NP out. Therefore, the puncturing procedure itself has been used to induce disc degeneration (Sobajima et al., 2005) where MRI signal reduction and disc height reduction, and complications such as herniation and osteophyte formation are evident. Most in vivo studies of MSC-based therapy in disc degeneration inject cells in hydrogel carriers such as hyaluronic acid (Crevensten et al., 2004), albumin/hyaluronan (Benz et al., 2012), atelocollagen (Sakai et al., 2006) and fibrin (Acosta et al., 2011). However, less than 1% of the labeled cells were detected in NP immediately after injection and a significant reduction of the injected cells was noted on day 7 even though hydrogel carrier was used (Crevensten et al., 2004). One primary reason is the disc pressure-induced extrusion of injected materials including MSCs and HA hydrogel outside the disc space (Crevensten et al., 2004). Moreover, a recent study injecting allogenic MSC to degenerative disc in rabbit reported formation of large osteophytes in all animals at 3 months post-injection (Vadala et al., 2012), corroborating with a previous report on osteophyte formation after MSC injection in healthy disc (Sobajima et al., 2008). Most importantly, labeled MSCs were not found in NP but within the osteophytes with endochondral ossification signs, providing evidences that the high intra-discal pressure may result in significant cell leakage during injection and the misdirected MSCs may contribute to the formation of osteophyte via chondrogenic differentiation (Vadala et al., 2012). These data suggest that cell leakage during intra-discal delivery of MSCs leads to undesired bone formation that may further deteriorate disc degeneration. This raises the concern on the undesirable side-effect or complication of MSC-based therapy in disc degeneration and suggests the significance of solving the cell leakage problem before clinical translation. Developing an annulus repair material mimicking the native annulus mechanical property, supportive to cell growth and that survives physiological strains has been suggested (Schek et al., 2011).

Disclosed herein is a method to alleviate the cell leakage problem and the associated complication, osteophyte formation by developing an injectable annulus plug to block the injection portal of MSCs during intra-discal injection. Our group has previously developed a patented photochemical crosslinking technology (Chan & So, 2008) to improve the physicochemical properties including mechanical strength, chemical stability and swelling property of collagen-based scaffolds (Chan & So, 2005; Chan et al., 2007; Chan, 2010). We also demonstrated that photochemically crosslinked collagen structures have excellent tissue compatibility and superb stability upon subcutaneous implantation (Chan et al., 2007). In addition, tangent modulus of photochemically crosslinked collagen membrane is of the same order of magnitude as compared with that of annulus lamellae (Sobajima et al., 2008; Zhao et al., 2007; Raj, 2008). These findings rationalized the development of a photochemically crosslinked collagen annulus plug to block the injection portal and reduce leakage. Specifically, we aim to (1) fabricate and optimize a photochemically crosslinked collagen annulus plug; (2) deliver the annulus plug intra-discally via injection; (3) evaluate its mechanical performance and effectiveness in reducing cell leakage ex vivo under compression and torsion push-out tests; and (4) conduct a pilot in vivo study in rabbits evaluating osteophyte formation complication and functional regeneration outcomes.

All references, including publications, patent applications and patents, cited herein are hereby incorporated by reference to the same extent as if each reference was individually and specifically indicated to be incorporated by reference and was set forth in its entirety herein.

It should be understood that the examples and embodiments described herein are for illustrative purposes only and that various modifications or changes in light thereof will be suggested to persons skilled in the art and are to be included within the spirit and purview of this application.

REFERENCES

Acosta F L Jr et al. Porcine intervertebral disc repair using allogeneic juvenile articular chondrocytes or mesenchymal stem cells. *Tissue eng Part A*. 2011; 17:3045-55.

Benz K, Stippich C, Fischer L, Mohl K, Weber K, Lang J, Steffen F, Beintner B, Gaissmaier C, Mollenhauer J A. Intervertebral disc cell- and hydrogel-supported and spontaneous intervertebral disc repair in nucleotomized sheep. *Eur Spine J.* 2012; 21(9):1758-68.

Bertram H, Kroeber M, Wang H,et al. Matrix-assisted cell transfer for interverte-bral disc cell therapy. *Biochem Biophys Res Commun.* 2005; 331:1185-1192.

Cauthen J C, (inventor); Anulex Technologies, Inc. (assignee): Spinal disc annulus reconstruction method and spinal disc annulus stent. U.S. Pat. No. 6,592,625. Jul. 15, 2003

Chan B P et al. Photochemical cross-linking for collagen-based scaffolds: a study on optical properties, mechanical properties, stability, and hematocompatibility. *Tissue eng.* 2007; 13:73-85.

Chan B P, So K F. Photochemical crosslinking improves the physicochemical properties of collagen scaffolds. *J Biomed Mater Res A.* 2005; 75:689-701.

Chan B P, So K F. Photochemically crosslinked collagen scaffolds and methods for their preparation. U.S. Pat. No. 7,393,437 (1 Jul. 2008).

Chan B P. Biomedical applications of photochemistry. *Tissue Eng Part B Rev.* 2010; 16:509-22.

Chang M C, Tanaka J. FT-IR study for hydroxyapatite/collagen nanocomposite cross-linked by glutaraldehyde. *Biomaterials.* 2002; 23:4811-8.

Cheng H W, Luk K D, Cheung K M, Chan B P. In vitro generation of an osteochondral interface from mesenchymal stem cell-collagen microspheres. *Biomaterials.* 2011; 32:1526-35.

Cheung K M C, Ho G, Chan D, Leung V Y L. Regeneration of nucleus pulposus after discectomy by autologous mesenchymal stem cells: a rabbit model. *Eur Cell Mater.* 2005; 10:52.

Ching C T, Chow D H, Yao F Y, Holmes A D. Changes in nuclear composition following cyclic compression of the intervertebral disc in an in vivo rat-tail model. *Med Eng Phys.* 2004; 26:587-94.

Chujo T, An H S, Akeda K, Miyamoto K, Muehleman C, Attawia M, Masuda K. Effects of growth differentiation factor-5 on the intervertebral disc—in vitro bovine study and in vivo rabbit disc degeneration model study. *Spine.* 2006; 31:2909-17.

Crevensten G, Walsh A J, Ananthakrishnan D, et al. Intervertebral disc cell therapy for regeneration: mesenchymal stem cell implantation in rat intervertebral discs. *Ann Biomed Eng.* 2004; 32(3):430-434.

Di Martino A, Vaccaro A R, Lee J Y, Denaro V, Lim M R. Nucleus pulposus replacement: basic science and indications for clinical use. *Spine.* 2005; 30:S16-22.

Ferree B: Artificial intervertebral disc replacement methods and apparatus. U.S. Pat. No. 6,419,704. Jul. 16, 2002

Freimark D, Czermak P. Cell-based regeneration of intervertebral disc defects: Review and concepts. *The International Journal of Artificial Organs.* 2009; 32(4):197-203.

Henriksson H B, Svanvik T, Jonsson M, Hagman M, Horn M, Lindahl A, Brisby H. Transplantation of human mesenchymal stems cells into intervertebral discs in a xenogeneic porcine model. *Spine.* 2009; 34:141-8.

Heuer F, Ulrich S, Claes L, Wilke H J. Biomechanical evaluation of conventional anulus fibrosus closure methods required for nucleus replacement. Laboratory investigation. *J Neurosurg Spine.* 2008; 9:307-13.

Ho G, Leung V Y, Cheung K M, Chan D. Effect of severity of intervertebral disc injury on mesenchymal stem cell-based regeneration. *Connect Tissue Res.* 2008; 49:15-21.

Illien-Junger S, Gantenbein-Ritter B, Grad S, et al. The Combined Effects of Limited Nutrition and High-Frequency Loading on Intervertebral Discs With Endplates. *Spine.* 2010; 35(19): 1744-1752.

Kong J, Yu S. Fourier transform infrared spectroscopic analysis of protein secondary structures. *Acta Biochim Biophys Sin.* 2007; 39:549-59.

Lambrecht G H, Moore R K, Banks T, Redmond R J, Vidal C A (inventors); Intrinsic Therapeutics, Inc. (assignee): Methods and apparatus for dynamically stable spinal implant. U.S. Pat. No. 6,883,520. Apr. 26, 2005

Leung V Y L, Chan D, Cheung K M C, Regeneration of intervertebral disc by mesenchymal stem cells: potentials, limitations, and future direction, *Eur Spine J.* 2006; 15 (Suppl.):S406-S413.

Maclean J J, Lee C R, Alini M, Iatridis J C. Anabolic and catabolic mRNA levels of the intervertebral disc vary with the magnitude and frequency of in vivo dynamic compression. *J Orthop Res.* 2004; 22:1193-200.

MacLean J J, Lee C R, Alini M, Iatridis J C. The effects of short-term load duration on anabolic and catabolic gene expression in the rat tail intervertebral disc. *J Orthop Res.* 2005; 23:1120-7.

Masuoka K, Michalek A J, MacLean J J, Stokes I A, Iatridis J C. Different effects of static versus cyclic compressive loading on rat intervertebral disc height and water loss in vitro. *Spine.* 2007; 32:1974-9.

Miyamoto T, Muneta T, Tabuchi T, Matsumoto K, Saito H, Tsuji K, Sekiya I. Intradiscal transplantation of synovial mesenchymal stem cells prevents intervertebral disc degeneration through suppression of matrix metalloproteinase-related genes in nucleus pulposus cells in rabbits. *Arthritis Res Ther.* 2010; 12:R206.

Raj P P. Intervertebral disc: anatomy-physiology-pathophysiology-treatment. *Pain Pract.* 2008; 8:18-44.

Risbud M V, Albert T J, Guttapalli A, Vresilovic E J, Hillibrand A S, Vaccaro A R, Shapiro M. Differentiation of mesenchymal stem cells towards a nucleus pulposus-like phenotype in vitro: implications for cell-based transplantation therapy. *Spine.* 2004; 29:2627-32.

Roberts S, Menage J, Sivan S, et al. Bovine explant model of degeneration of the intervertebral disc. *BMC Musculoskelet Disord.* 2008; 9:24.

Sakai D et al. Regenerative effects of transplanting mesenchymal stem cells embedded in atelocollagen to the degenerated intervertebral disc. *Biomaterials.* 2006; 27:335-45.

Sakai D et al. Transplantation of mesenchymal stem cells embedded in Atelocollagen gel to the intervertebral disc: a potential therapeutic model for disc degeneration. *Biomaterials.* 2003; 24:3531-41.

Sakai D, Mochida J, Iwashina T, Watanabe T, Nakai T, Ando K, Hotta T. Differentiation of mesenchymal stem cells transplanted to a rabbit degenerative disc model: potential and limitations for stem cell therapy in disc regeneration. *Spine.* 2005 Nov. 1; 30(21):2379-87.

Schek R M, Michalek A J, Iatridis J C. Genipin-crosslinked fibrin hydrogels as a potential adhesive to augment intervertebral disc annulus repair. *Eur Cell Mater.* 2011; 21:373-83.

Sobajima S et al. A slowly progressive and reproducible animal model of intervertebral disc degeneration characterized by MRI, X-ray, and histology. *Spine.* 2005; 30:15-24.

Sobajima S, Kompel J F, Kim J S, et al. A slowly progressive and reproducible animal model of intervertebral disc degeneration characterized by MRI, X-ray, and histology. *Spine* (Phila Pa. 1976). 2004; 30:15-24.

Sobajima S, Vadala G, Shimer A et al. Feasibility of a stem cell therapy for intervertebral disc degeneration. *Spine J.* 2008; 8(6):888-96.

Sykova E, Jendelova P, Urdzikova L, Lesny P, Hejcl A. Bone Marrow Stem Cells and Polymer Hydrogels—Two Strategies for Spinal Cord Injury Repair. *Cell Mol Neurobiol.* 2006 Apr. 22

Vadala G, Sowa G, Hubert M, Gilbertson L G, Denaro V, Kang J D. Mesenchymal stem cells injection in degenerated intervertebral disc: cell leakage may induce osteophyte formation. *J Tissue Eng Regen Med.* 2012; 6:348-55.

Vadala G, Sowa G W, Hubert M, et al. Mesenchymal stem cells injection in degenerated intervertebral disc: cell leakage may induce osteophyte formation. *J Tissue Eng Regen Med.* 2011; DOI:10.1002/term.433.

Vadalà G, Studer R K, Sowa G, et al. Coculture of bone marrow mesenchymal stem cells and nucleus pulposus cells modulate gene expression profile without cell fusion. *Spine* (Phila Pa. 1976). 2008; 33(8):870-876.

Wang D L, Jiang S D, Dai L Y. Biologic response of the intervertebral disc to static and dynamic compression in vitro. *Spine.* 2007; 32:2521-8.

Yang F, Leung V Y, Luk K D, Chan D, Cheung K M. Mesenchymal stem cells arrest intervertebral disc degeneration through chondrocytic differentiation and stimulation of endogenous cells. *Mol Ther.* 2009; 17:1959-66.

Yoshikawa T., Ueda, Y., Miyazaki, K., et al. Disc Regeneration Therapy Using Marrow Mesenchymal Cell Transplantation A Report of Two Case Studies. *Spine.* 2010; 35:E475-E480

Zhang Y G, Guo X, Xu P et al., Bone mesenchymal stem cells transplanted into rabbit intervertebral discs can increase proteoglycans, *Clin Orthop Relat Res.* 2005; 430:219-26.

Zhao C Q, Wang L M, Jiang L S, Dai L Y. The cell biology of intervertebral disc aging and degeneration. *Ageing Res Rev.* 2007; 6:247-61.

What is claimed is:

1. A method for preventing leakage of therapeutic agents from a target site in an annulus of an intervertebral disc through an injection opening created by an injection needle, the injection opening having a certain length, wherein the method comprises:
    delivering the therapeutic agents to the target site in a subject using an apparatus while creating the injection opening adjacent to the target site, the injection opening comprising an exterior end, wherein the apparatus comprises the injection needle comprising a plunger, and a transparent tubing connecting a first detachable portion with the injection needle;
    closing the tubing;
    removing the first detachable portion from the tubing;
    attaching a second detachable portion comprising a needle shaped plug to the tubing;
    marking the second detachable portion to indicate the length of the injection opening;
    opening the tubing;
    delivering the needle shaped plug to fill the injection opening by pushing the injection needle plunger and stopping at the marking of the second detachable portion,
    removing the apparatus; and
    applying a biocompatible adhesive to the exterior end of the injection opening.

2. The method according to claim 1, wherein the therapeutic agents comprise mesenchymal stem cell suspension.

3. The method according to claim 1, wherein the needle shaped plug is made of biocompatible material comprising photochemically crosslinked type I collagen matrix, collagen and glycosaminoglycan (GAG) composite, or a combination thereof.

4. The method according to claim 1, further comprising positioning the needle shaped plug inside the injection opening.

5. The method according to claim 1, wherein the needle shaped plug is in a dehydrated state before injection into the subject, and the filling device takes the shape that can substantially fill the artificially-created opening by hydration.

6. The method according to claim 1, wherein the needle shaped plug is made of biocompatible material.

* * * * *